United States Patent
Gilmore et al.

(10) Patent No.: US 9,913,854 B2
(45) Date of Patent: Mar. 13, 2018

(54) METHODS AND COMPOSITIONS FOR REDUCING THE PROLIFERATION OF GRAM POSITIVE BACTERIA

(71) Applicant: MASSACHUSETTS EYE & EAR INFIRMARY, Boston, MA (US)

(72) Inventors: Michael S. Gilmore, Boston, MA (US); Takashi Suzuki, Matsumyama (JP)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 14/388,685

(22) PCT Filed: Mar. 14, 2013

(86) PCT No.: PCT/US2013/031590
§ 371 (c)(1),
(2) Date: Sep. 26, 2014

(87) PCT Pub. No.: WO2013/148269
PCT Pub. Date: Oct. 3, 2013

(65) Prior Publication Data
US 2015/0087614 A1    Mar. 26, 2015

Related U.S. Application Data

(60) Provisional application No. 61/616,530, filed on Mar. 28, 2012.

(51) Int. Cl.
| | |
|---|---|
| *A61K 31/706* | (2006.01) |
| *A61K 31/655* | (2006.01) |
| *A01N 43/54* | (2006.01) |
| *A01N 33/26* | (2006.01) |
| *C07D 405/14* | (2006.01) |
| *C09B 23/14* | (2006.01) |
| *C09B 29/01* | (2006.01) |
| *C09B 29/095* | (2006.01) |
| *C09B 31/043* | (2006.01) |
| *C09B 33/056* | (2006.01) |
| *C09B 33/16* | (2006.01) |
| *C09B 67/36* | (2006.01) |
| *C09B 67/02* | (2006.01) |
| *A61K 45/06* | (2006.01) |
| *A61K 31/7072* | (2006.01) |

(52) U.S. Cl.
CPC ........... *A61K 31/706* (2013.01); *A01N 33/26* (2013.01); *A01N 43/54* (2013.01); *A61K 31/655* (2013.01); *A61K 31/7072* (2013.01); *A61K 45/06* (2013.01); *C07D 405/14* (2013.01); *C09B 23/148* (2013.01); *C09B 29/0014* (2013.01); *C09B 29/0955* (2013.01); *C09B 31/043* (2013.01); *C09B 33/056* (2013.01); *C09B 33/16* (2013.01); *C09B 67/0079* (2013.01); *C09B 67/0097* (2013.01)

(58) Field of Classification Search
CPC . C07D 405/14; C09B 23/148; C09B 29/0014; C09B 29/0955; C09B 31/043; C09B 33/056; C09B 33/16; C09B 67/0079; C09B 67/0097; A61K 45/06; A61K 31/655; A61K 31/7072; A61K 31/706; A61K 2300/00; A01N 33/26; A01N 43/54
USPC ........ 514/50; 435/252.1, 252.5, 252.7, 253.4
See application file for complete search history.

(56) References Cited

U.S. PATENT DOCUMENTS

| | | | |
|---|---|---|---|
| 4,330,624 A | 5/1982 | Tejera et al. | |
| 4,336,333 A | 6/1982 | Hamill et al. | |

FOREIGN PATENT DOCUMENTS

| | | | | |
|---|---|---|---|---|
| CN | 1880378 | * | 12/2006 | ............. C09B 29/36 |
| JP | S6150995 | | 3/1986 | |

OTHER PUBLICATIONS

Takatsuki et al, The Journal of Antibiotics, 1971, 24(4), 215-223.*
Wainwright, Dyes and Pigments 92008, 76, 583-589.*
International Search Report and Written Opinion in International Application No. PCT/US2013/031590, dated Jul. 4, 2013, 6 pages.
International Preliminary Report on Patentability in International Application No. PCT/US2013/031590, dated Oct. 1, 2014, 5 pages.
Campbell et al., "Synthetic lethal compound combinations reveal a fundamental connection between wall teichoic acid and peptidoglycan biosyntheses in *Staphylococcus aureus*," ACS Chem. Biol., 6:106-116 (Jan. 21, 2011) (Author Manuscript).
Caspi et al., "The Anti-prion Activity of Congo Red. Putative mechanism," J Biol Chem., 273(6):3484-3489 (Feb. 6, 1998).
Centers for Disease Control and Prevention, "From the Centers for Disease Control and Prevention. Four pediatric deaths from community-acquired methicillin-resistant *Staphylococcus aureus*—Minnesota and North Dakota, 1997-1999," JAMA, 282(12):1123-1125 (Sep. 22-29, 1999).
Chang et al., "Infection with vancomycin-resistant *Staphylococcus aureus* containing the vanA resistance gene," N Engl. J. Med., 348:1342-1347 (Apr. 3, 2003).
Dictionary of Antibiotics and Related Substances, 1:714-715 (1988).

(Continued)

*Primary Examiner* — Ganapathy Krishnan
(74) *Attorney, Agent, or Firm* — Fish & Richardson P.C.

(57) ABSTRACT

Provided herein are methods for inducing cell death in a gram positive bacterium and methods for reducing the proliferation of a gram positive bacterium that include contacting a gram positive bacterium with a dye (e.g., an azo dye) and a TarO inhibitor. Also provided are methods of treating a subject having a gram positive bacterial infection that include administering to a subject having a gram positive bacterial infection a dye (e.g., an azo dye) and a TarO inhibitor. Also provided are compositions containing a dye (e.g., an azo dye) and a TarO inhibitor, and kits containing at least one of these compositions.

15 Claims, 16 Drawing Sheets
(8 of 16 Drawing Sheet(s) Filed in Color)

(56) References Cited

OTHER PUBLICATIONS

Domagk, Deutsche Med. Wochschr. 61;250-253 (1935) (English Abstract).
Duksin and Mahoney, "Relationship of the structure and biological activity of the natural homologues of tunicamycin," J. Biol. Chem., 257:3105-3109 (Mar. 25, 1982).
Duthie and Lorenz, "Staphylococcal coagulase; mode of action and antigenicity," J. Gen. Microbial., 6:95-107 (Feb. 1952).
Grundling and Schneewind, "Cross-linked peptidoglycan mediates lysostaphin binding to the cell wall envelope of *Staphylococcus aureus*," J. Bacterial., 188:2463-2472 (Apr. 2006).
Grundling and Schneewind, "Synthesis of glycerol phosphate lipoteichoic acid in *Staphylococcus aureus*," Proc. Natl. Acad. Sci. US.A., 104:8478-8483 (May 15, 2007).
Hancock et al., "Biosynthesis of the unit that links teichoic acid to the bacterial wall: inhibition by tunicamycin," FEBS Lett., 69:75-80 (Oct. 15, 1976).
Horlein, "The Chemotherapy of Infectious Diseases caused by Protozoa and Bacteria: (Section of Tropical Diseases and Parasitology)," Proc. Royal Soc. Med., 29:313-324 (Feb. 1936).
Hubscher et al., "MsrR contributes to cell surface characteristics and virulence in *Staphylococcus aureus*," FEMS Microbiol. Lett., 295:251-260 (Jun. 2009).
Ito et al., "Isolation and Structures of Components of Tunicamycin," Agric. Biol. Chem. 44:695-698 (1980).
Kenig and Reading, "Holomycin and an antibiotic (MM 19290) related to tunicamycin, metabolites of Streptomyces clavuligerus," J. Antibiot. (Tokyo), 32:549-554 (Jun. 1979).
Klee et al., Deut. Med. Wochschr. 61:253-355 (1935) (English Abstract).
Kreiswirth et al., "The toxic shock syndrome exotoxin structural gene is not detectably transmitted by a prophage," Nature, 305:709-712 (Oct. 20-26, 1983).
Mahoney et al., "Separation of tunicamycin homologues by reversed-phase high-performance liquid chromatography," J. Chromatogr., 198:506-510 (Oct. 24, 1980).
Meredith et al., "Late-stage polyribitol phosphate wall teichoic acid biosynthesis in *Staphylococcus aureus*," J. Bacteriol., 190:3046-3056 (Apr. 2008).
Moller and Wallin, "Genotoxic hazards of azo pigments and other colorants related to 1-phenylazo-2-hydroxynaphthalene," Mutat. Res., 462:13-30 (Jan. 2000).
Morin and Bernacki, "Biochemical effects and therapeutic potential of tunicamycin in murine L1210 leukemia," Cancer Res., 43:1669-1674 (Apr. 1983).
Neuhaus and Baddiley, "A continuum of anionic charge: structures and functions of D-alanyl-teichoic acids in gram-positive bacteria," Microbiol. Mol. Biol. Rev. 67:686-723 (Dec. 2003).
Oku et al., "Pleiotropic roles of polyglycerolphosphate synthase of lipoteichoic acid in growth of *Staphylococcus aureus* cells," J. Bacterial., 191:141-151 (Jan. 2009).
Peng et al., "Cloning, characterization, and sequencing of an accessory gene regulator (agr) in *Staphylococcus aureus*," J. Bacterial., 170:4365-4372 (Sep. 1988).
Price and Tsvetanova, "Biosynthesis of the tunicamycins: a review," J. Antibiot., 60:485-491 (Aug. 2007).
Suzuki et al., "In vitro antimicrobial activity of wall teichoic acid biosynthesis inhibitors against *Staphylococcus aureus* isolates," Antimicrob. Agents Chemother., 55:767-774 (Feb. 2011).
Suzuki et al., "Role of Wall Teichoic Acids in *Staphylococcus aureus* Endophthalmitis," Invest Ophthalmol Vis Sci., 52(6):3187-92 (May 16, 2011).
Swoboda et al., "Discovery of a small molecule that blocks wall teichoic acid biosynthesis in *Staphylococcus aureus*," ACS Chem. Biol., 4:875-883 (Oct. 16, 2009).
Swoboda et al., "Wall Teichoic Acid Function, Biosynthesis, and Inhibition," Chembiochem., 11(1):35-45 (Jan. 4, 2010) (Author Manuscript).
Takatsuki et al., "Tunicamycin, a new antibiotic. I. Isolation and characterization of tunicamycin," J. Antibiot., 24:215-223 (Apr. 1971).
Wainwright, "Dyes in the development of drugs and pharmaceuticals," Dyes and Pigments, 76:582-589 (2008).
Weidenmaier and Peschel, "Teichoic acids and related cell-wall glycopolymers in Gram-positive physiology and host interactions," Nature, 6:276-287 (Apr. 2008).
Weidenmaier et al., "Differential roles of sortase-anchored surface proteins and wall teichoic acid in *Staphylococcus aureus* nasal colonization," Int. J. Med. Microbiol., 298:505-513 (Jul. 2008).
Weidenmaier et al., "Lack of wall teichoic acids in *Staphylococcus aureus* leads to reduced interactions with endothelial cells and to attenuated virulence in a rabbit model of endocarditis," J. Infect. Dis., 191:1771-1777 (May 15, 2005).
Weidenmaier et al., "Role of teichoic acids in *Staphylococcus aureus* nasal colonization, a major risk factor in nosocomial infections," Nat. Med., 10:243-245 (Mar. 2004).
Suzuki et al., "Wall teichoic acid protects *Staphylococcus aureus* from inhibition by Congo red and other dyes," J. Antimicrob Chemother, 67: 2143-2151, 2012.
Material Safety Data Sheet, Santa Cruz Biotechnology Inc., Tunicamycin, sc-3506, Apr. 3, 2010.

\* cited by examiner

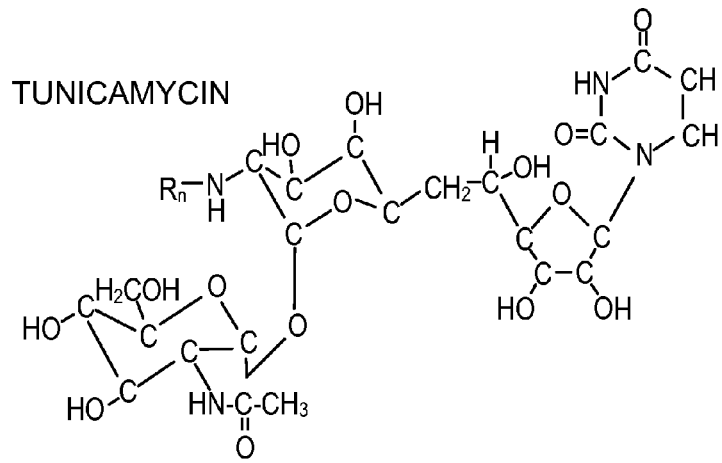

| | | | |
|---|---|---|---|
| $(CH_3)_2\text{-}CH\text{-}(CH_2)_7\text{-}CH=CH\text{-}\overset{O}{\underset{\|}{C}}\text{-}$ | $(C_{13})$ | $A_0$ | $\alpha, \beta$ unsaturated trans iso |
| $(CH_3)_2\text{-}CH\text{-}(CH_2)_8\text{-}CH=CH\text{-}\overset{O}{\underset{\|}{C}}\text{-}$ | $(C_{14})$ | $A_1$ | $\alpha, \beta$ unsaturated trans iso |
| $CH_3\text{-}(CH_2)_{10}\text{-}CH=CH\text{-}\overset{O}{\underset{\|}{C}}\text{-}$ | $(C_{14})$ | $A_2$ | $\alpha, \beta$ unsaturated trans normal |
| $C_{12}\text{-}H_{25}\text{-}CH=CH\text{-}\overset{O}{\underset{\|}{C}}\text{-}$ | $(C_{15})$ | $B_1$ | |
| $(CH_3)_2\text{-}CH\text{-}(CH_2)_9\text{-}CH=CH\text{-}\overset{O}{\underset{\|}{C}}\text{-}$ | $(C_{15})$ | $B_2$ | $\alpha, \beta$ unsaturated trans normal |
| $(CH_3)_2\text{-}CH\text{-}(CH_2)_{11}\text{-}\overset{O}{\underset{\|}{C}}\text{-}$ | $(C_{15})$ | $B_3$ | saturated iso |
| $(CH_3)_2\text{-}CH\text{-}(CH_2)_{10}\text{-}CH=CH\text{-}\overset{O}{\underset{\|}{C}}\text{-}$ | $(C_{16})$ | $C_1$ | $\alpha, \beta$ unsaturated trans iso |
| $CH_3\text{-}(CH_2)_{12}\text{-}CH=CH\text{-}\overset{O}{\underset{\|}{C}}\text{-}$ | $(C_{16})$ | $C_2$ | $\alpha, \beta$ unsaturated trans normal |
| $C_{14}H_{29})\text{-}CH=CH\text{-}\overset{O}{\underset{\|}{C}}\text{-}$ | $(C_{17})$ | $D_1$ | |
| $(CH_3)_2\text{-}CH\text{-}(CH_2)_{11}\text{-}CH=CH\text{-}\overset{O}{\underset{\|}{C}}\text{-}$ | $(C_{17})$ | $D_2$ | $\alpha, \beta$ unsaturated trans iso |

FIG. 2

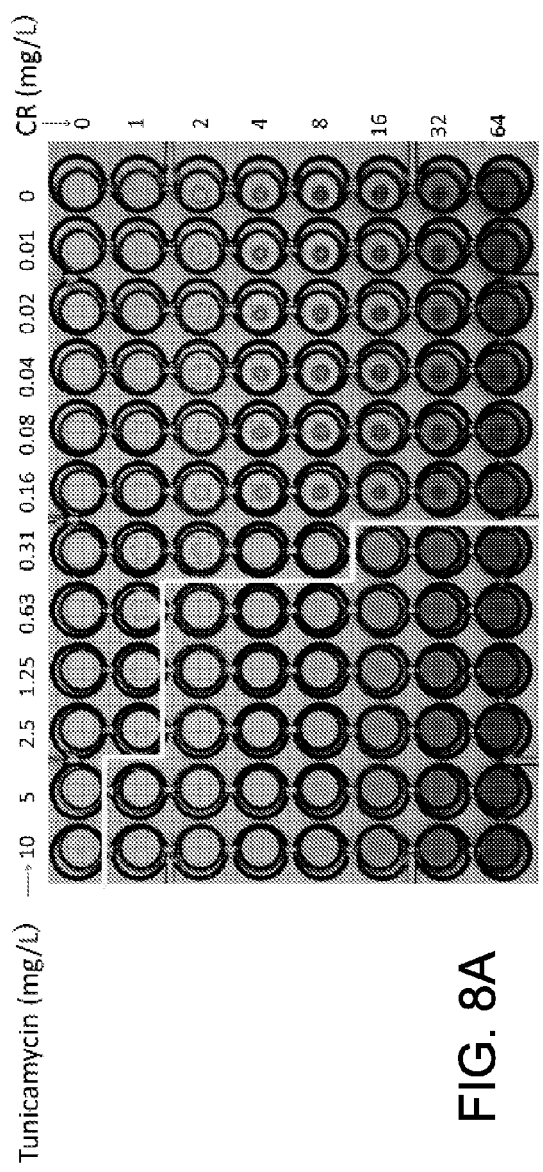
FIG. 8A
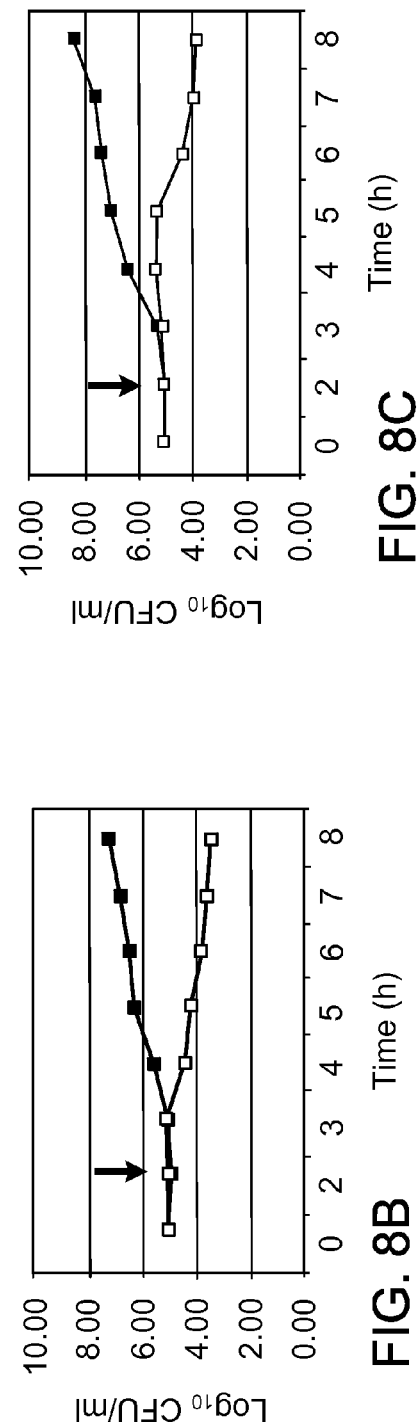
FIG. 8B
FIG. 8C

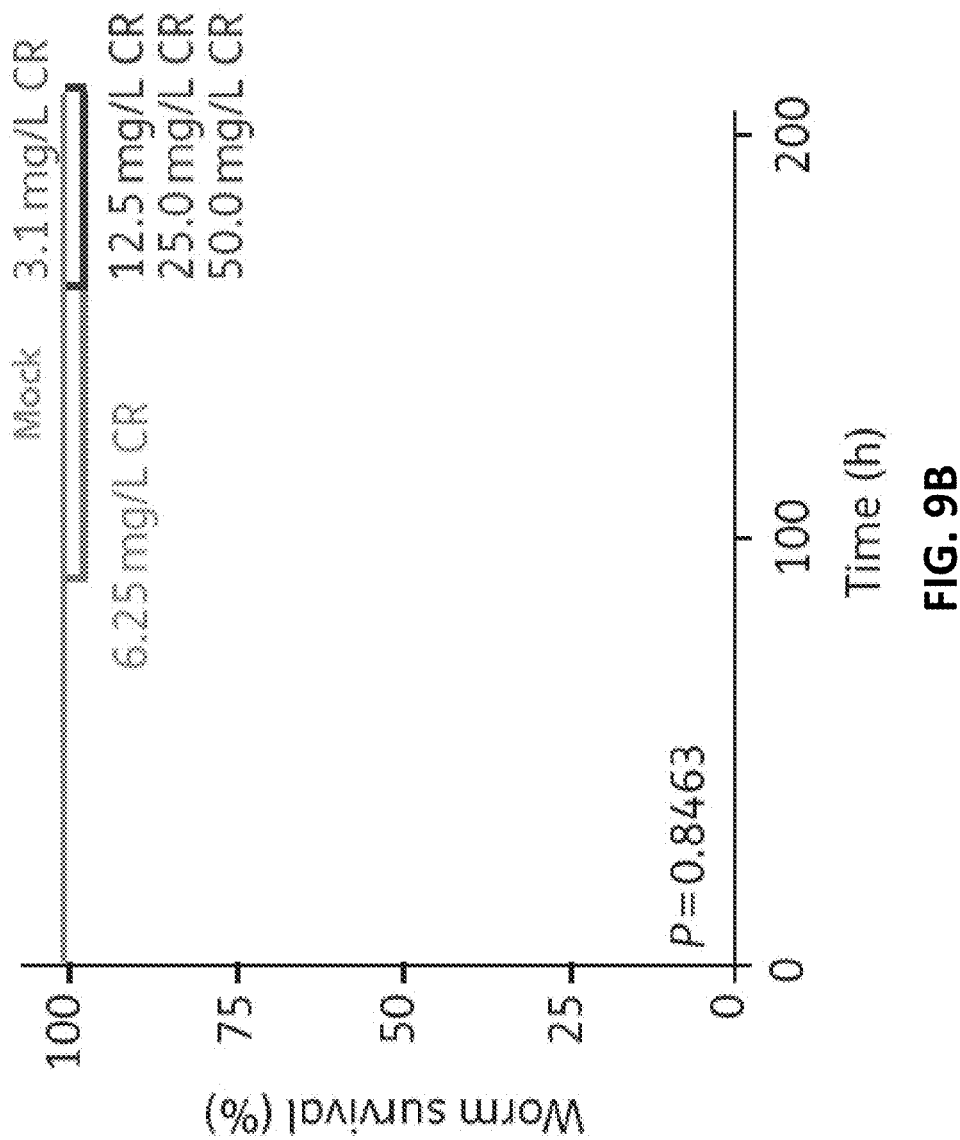

METHODS AND COMPOSITIONS FOR REDUCING THE PROLIFERATION OF GRAM POSITIVE BACTERIA

CROSS-REFERENCE TO RELATED APPLICATIONS

This application is the National Stage of International Patent Application No. PCT/US2013/031590, filed on Mar. 14, 2013, which claims priority to U.S. Provisional Patent Application Ser. No. 61/616,530, filed on Mar. 28, 2012, the entire contents of which are incorporated by reference herein.

FEDERALLY SPONSORED RESEARCH

This invention was made with Government support under grant numbers AI083214 and EY017381 awarded by the National Institutes of Health. The Government has certain rights in the invention.

BACKGROUND OF THE INVENTION

Gram positive bacterial infections afflict humans around the world. For example, *Staphylococcus aureus* is a leading pathogen of community and hospital acquired infection of the skin, soft tissues, and other sites (Fridkin et al., *N. Engl. J. Med.* 352:1436-1444, 2005; Tenover et al., *J. Antimicrob. Chemother.* 64:441-446, 2009). Compounding the problem is antibiotic resistance, which initially developed in hospitals, but has since spread to the community where rates of methicillin-resistant *S. aureus* (MRSA) are now approaching those in hospitals (Fridkin et al., *N. Engl. J. Med.* 352:1436-1444, 2005; Tenover et al., *J. Antimicrob. Chemother.* 64:441-446, 2009).

The gram positive *S. aureus* cell wall includes two negatively charged polymers: lipoteichoic acid (LTA) and wall teichoic acid (WTA), which form a highly hydrated polyanionic matrix that is interwoven through the peptidoglycan. While not all gram-positive bacteria have teichoic acid polymers identical to those of *S. aureus*, alternate polymers generally have functional similarity and anionic character, indicating that anionic polymers are central to the normal function of the gram positive cell wall (Neuhaus et al., *Microbiol. Mol. Biol. Rev.* 67:686-723, 2003). WTAs are phosphate-rich, carbohydrate-based polymers, which are initially synthesized on a lipid carrier inserted into the inner leaf of the cytoplasmic membrane, before being transported to the cell surface where they are covalently linked to peptidoglycan (Swoboda et al., *ChemBioChem* 11:35-45, 2010). WTAs affect cation binding, tensile strength, rigidity, and porosity of the gram positive cell wall (Swoboda et al., *ChemBioChem* 11:35-45, 2010). They are essential for normal *S. aureus* adherence to epithelial and endothelial cells, and virulence (Suzuki et al., *Invest. Ophthalmol. Vis. Sci.* 52:3187-3192, 2011; Suzuki et al., *Antimicrob. Agents Chemother.* 55:767-774, 2011; Weidenmaier et al., *Nat. Med.* 10:243-245, 2004; Weidenmaier et al., *Int. J. Med. Microbiol.* 298:515-513, 2008; Weidenmaier et al., *Nat. Rev. Microbiol.* 6:276-287, 2008; Weidenmaier et al., *J. Infect. Dis.* 191:1771-1777, 2005).

SUMMARY OF THE INVENTION

The invention is based, in part, on the discovery that the combination of a dye (e.g., an azo dye, such as an anionic azo dye) and a TarO inhibitor (e.g., a tunicamycin or tunicamycin derivative) decrease the proliferation of gram positive bacteria. In view of this discovery, provided herein are methods for inducing cell death in a gram positive bacterium and methods for reducing the proliferation of a gram positive bacterium that include contacting a gram positive bacterium with a dye (e.g., an azo dye, such as an anionic azo dye) and a TarO inhibitor. Also provided are methods of treating a subject having a gram positive bacterial infection that include administering to a subject having a gram positive bacterial infection a dye (e.g., an azo dye, such as an anionic azo dye) and a TarO inhibitor (e.g., a tunicmycin or a tunicamycin derivative). Also provided are compositions (e.g., any of the exemplary compositions described herein) containing a dye (e.g., an azo dye, such as an anionic azo dye) and a TarO inhibitor (e.g., a tunicamycin or a tunicamycin derivative), and kits containing at least one of these compositions.

Provided herein are methods for inducing cell death in a gram positive bacterium that include contacting a gram positive bacterium with an azo dye and a TarO inhibitor in amounts sufficient to induce cell death in the gram positive bacterium. Also provided are methods for reducing the proliferation of gram positive bacterium that include contacting a gram positive bacterium with an azo dye and a TarO inhibitor in amounts sufficient to reduce the proliferation of the gram positive bacterium. In some embodiments, the gram positive bacterium is present in a mammal (e.g., a human). In some embodiments, the gram positive bacterium is present in vitro. In some embodiments, the gram positive bacterium is present in a cell culture, present in or on a food composition, or present in a pharmaceutical or cosmetic composition.

In some embodiments, the gram positive bacterium is an antibiotic-resistant gram positive bacterium. In some embodiments, the gram positive bacterium is a *coccus* gram positive bacterium (e.g., a *coccus* gram positive bacterium from the *Streptococcus, Enterococcus*, or *Staphylococcus* genus). In some embodiments, the *coccus* gram positive bacterium is *Staphylococcus aureus* (e.g., a methicillin-resistant *Staphylococcus aureus*). In some embodiments, the gram positive bacterium is a *bacillus* gram positive bacterium (e.g., a *bacillus* gram positive bacterium from the *Cornebacterium, Listeria, Bacillus*, or *Clostridium* genus). In some embodiments, the azo dye and the TarO inhibitor are formulated in a single composition.

Also provided are methods of treating a subject having a gram positive bacterial infection that include administering to a subject having a gram positive bacterial infection an azo dye and a TarO inhibitor in amounts sufficient to decrease the population of gram positive bacteria in the subject. In some embodiments, the population of gram positive bacteria includes antibiotic-resistant gram positive bacteria. In some embodiments, the population of gram positive bacteria includes *coccus* gram positive bacteria. In some embodiments, the gram positive bacteria are from the *Streptococcus, Enterococcus*, or *Staphylococcus* genus. In some embodiments, the *coccus* gram positive bacteria are *Staphylococcus aureus* (e.g., methicillin-resistant *Staphylococcus aureus*). In some embodiments, the population of gram positive bacteria includes *bacillus* gram positive bacteria. In some embodiments, the *bacillus* gram positive bacteria are from the *Cornebacterium, Listeria, Bacillus*, or *Clostridium* genus.

In some embodiments of the methods described herein, the azo dye is selected from the group of Congo Red, Sudan Red, Direct Red, Mordant black, and Acid Red 88. In some embodiments, the azo dye is Congo Red. In some embodiments, the TarO inhibitor is a tunicamycin. In some embodiments, the azo dye is Congo Red and the TarO inhibitor is a tunicamycin.

In some embodiments, the azo dye and/or TarO inhibitor is formulated for oral, nasal, intravenous, intraarterial, topical, optical, subcutaneous, intramuscular, or intraperitoneal administration. In some embodiments, the azo dye and the TarO inhibitor are formulated in a single composition (e.g., a composition formulated for oral, intravenous, intraarterial, nasal, topical, optical, subcutaneous, intramuscular, or intraperitoneal administration). In some embodiments, the composition containing the azo dye and the TarO inhibitor is formulated for oral administration.

In some embodiments, the azo dye and/or the TarO inhibitor is administered by oral, intravenous, intraarterial, nasal, topical, optical, subcutaneous, intramuscular, or intraperitoneal administration. In some embodiments, the subject is a human. Some embodiments further include administering at least one additional antimicrobial agent.

Also provided are compositions including an azo dye; and a TarO inhibitor. In some embodiments, the composition is formulated in a dosage form that contains the azo dye and the TarO inhibitor in amounts sufficient to induce cell death or reduce proliferation in a gram positive bacterium present in or on a subject. In some embodiments, the composition is formulated in a dosage form that contains the azo dye and the TarO inhibitor in amounts sufficient to decrease the population of gram positive bacteria in or on a subject. In some embodiments of the compounds, the azo dye is selected from the group consisting of: Congo Red, Sudan Red, Direct Red, Mordant black, and Acid Red 88. In some embodiments of the compounds, the azo dye is Congo Red. In some embodiments of the compounds, the TarO inhibitor is a tunicamycin. In some embodiments of the compounds, the TarO inhibitor is tunicamycin and the azo dye is Congo Red. Some embodiments of the compositions further include at least one additional antimicrobial agent.

Also provided are kits containing at least one dose of any of the compositions described herein.

By the term "gram positive bacterium" or "gram positive bacteria" is meant a bacterium or bacteria that contain(s) teichoic acid (e.g., lipoteichoic acid and/or wall teichoic acid), or a functionally equivalent glycopolymer (e.g., a rhamnopolysaccharide, teichuronic acid, arabinogalactan, lipomannan, and lipoarabinomannan) in its cell wall. Non-limiting examples of functionally equivalent glycopolymers are described in Weidenmaier et al., Nature 6:276-287, 2008. Additional examples of functionally equivalent glycopolymers are known in the art. In some embodiments, a gram positive bacterium is identified using the Gram staining method (e.g., generally including the steps of staining with crystal violet, treating with an iodine solution, decolorizing with alcohol, and counterstaining with safranine, wherein a gram positive bacterium retains the violet stain). Non-limiting examples of gram positive bacteria are described herein. Additional examples of gram positive bacteria are known in the art. Exemplary methods for detecting or identifying a gram positive bacteria are described herein. Additional methods for detecting or identifying a gram positive bacteria are known in the art.

By the term "gram positive bacterial infection" is meant a pathological condition that is caused or mediated by the presence of a population of gram positive bacteria in a subject. Non-limiting examples of gram positive bacteria that can cause a gram positive bacterial infection are described herein. Additional examples of gram positive bacteria that can cause a gram positive bacterial infection are known in the art. In some embodiments, a gram positive bacterial infection can be a systemic infection or a local infection. In some embodiments, a gram positive bacterial infection can also be an acute gram positive bacterial infection or a chronic gram positive bacterial infection. In some embodiments, the gram positive bacterial infection is caused by an antibiotic-resistant gram positive bacterium (e.g., any of the antibiotic-resistant gram positive bacteria described herein or known in the art).

By the term "population of gram positive bacteria" is meant a two or more (e.g., ten or more, 100 or more, 500 or more, $10^3$ or more, $10^4$ or more, $10^6$ or more, $10^8$ or more, or $10^{10}$ or more) gram positive bacteria (e.g., two or more gram positive bacteria from the same genus and/or species, or two or more gram positive bacteria from different genera and/or species). A population of gram positive bacteria can include any (or any combination) of the gram positive bacteria described herein or known in the art. In some embodiments, a population of gram positive bacteria contains an antibiotic-resistant gram positive bacterium (e.g., any of the antibiotic-resistant bacteria described herein or known in the art).

By the term "proliferation" is meant the result of cell division of a gram positive bacterium or a population of gram positive bacteria, e.g., an increase in the total amount of gram positive bacteria present in a subject (e.g., in a biological sample from a subject) or a sample (e.g., a cell culture medium, a storage medium, a food composition (or an ingredient thereof), a pharmaceutical composition, or a cosmetic composition) at a later time point compared to an earlier time point. In some embodiments, the proliferation of a gram positive bacterium or a population of gram positive bacteria can be determined by detecting the number of gram positive bacteria present in a biological sample of a subject and comparing the number of gram positive bacteria present in the sample to a reference value (e.g., a number of gram positive bacteria present in a sample from the subject gathered at an earlier time point or the number of gram positive bacteria present in a sample from a healthy subject). In some embodiments, the presence or proliferation of a gram positive bacterium or a population of gram positive bacteria in a subject can be assessed indirectly by detecting or assessing the number of symptoms of a gram positive bacterial infection in a subject, or the severity, duration, or frequency of symptoms of a gram positive bacterial infection in a subject.

By the term "dye" is meant an organic compound that contains two or more conjugated carbon-carbon double bonds in linear and/or ring arrangement(s), and absorbs light at a visible wavelength (e.g., an absorption wavelength between 390 nm to 750 nm) or absorbs light at an ultraviolet wavelength (e.g., an absorption wavelength between 10 nm and 400 nm) and transmits remaining wavelengths of light, resulting in a visually- or instrumentally-detected change in color, or fluoresces by emitting light a different wavelength (e.g., an emission wavelength). Non-limiting examples of these compounds are dyes used in the food industry (e.g., Food Drug and Cosmetic Act (FD&C) Red dye #40 and FD&C Blue #1), in the pharmaceutical or cosmetics industry, and in the textile industry. In some embodiments, a dye is an azo-containing dye, such as Congo Red. In some embodiments, the dye lacks an azo bond but contains a conjugated carbon-carbon bond system (e.g., including two or more (e.g., three, four, five, or six) double bonds) (e.g., Calcofluor White) that contribute to their spectral and fluorescent properties. In some embodiments, the conjugated carbon-carbon bond system includes an aryl ring. In some embodiments, the conjugated carbon-carbon bond system includes a linear or branched carbon chain that contains two or more alternating carbon-carbon double bonds with electrons resonating in a π cloud.

By the term "azo dye" is meant a molecule containing the structure R—N=N—R'. In some embodiments, the azo dye has a net negative charge at a neutral pH (pH of ~7.0 to ~7.4) (i.e., an anionic azo dye). In some embodiments, the anionic azo dye contains one or more (e.g., two, three, four, or five) sulfonic acid groups or carboxylic acid groups. In some embodiments, the azo dye contains at least one (e.g., at least two, three, or four) aryl (e.g., phenyl) ring. Non-limiting examples of azo dyes are described herein. Additional examples of azo dyes are known in the art. In some embodiments, an azo dye can be administered or formulated as a salt.

By the term "TarO inhibitor" or "teichoic acid ribotol O inhibitor" is meant a molecule that reduces (e.g., a significant, detectable, or observable decrease) an activity of the protype S. aureus TarO polypeptide or a TarO homologue as found in other gram positive bacteria (e.g., addition of an activated sugar to the bactoprenol carrier) (e.g., in vitro or in vivo). Non-limiting examples of TarO homologues include enterococcal polysaccharide antigen (Epa) A proteins from E. faecalis or E. faecium (e.g., described in Palmer et al., mBio 3:e00318-11, 2012). Non-limiting examples of TarO inhibitors include the tunicamycins and tunicamycin derivatives described herein. Additional examples of TarO inhibitors are known in the art. Non-limiting exemplary methods for measuring an activity of TarO or a TarO homologue are described herein. Additional methods for measuring the activity of TarO or a TarO homologue are known in the art (see, e.g., Swoboda et al., ChemBioChem 11:35-45, 2010).

By the term "antibiotic-resistant gram positive bacterium" or "antibiotic-resistant gram positive bacteria" is meant a gram positive bacterium or bacteria that have a detectable, observable, or significant decrease in their sensitivity to one or more antimicrobial agents (e.g., methicillin, vancomycin, fluoroquinolone antibiotics (e.g., ciprofloxacin and/or levofloxacin)) as compared to another bacterium of the same genus or species. In some embodiments, the antibiotic-resistant gram positive bacterium is resistant to multiple antibiotics (a multi-drug resistant (MDR) gram positive bacterium). Non-limiting examples of antibiotic-resistant gram positive bacteria are described herein. Additional examples of gram positive antibiotic-resistant gram positive bacteria are known in the art.

By the term "anti-inflammatory agent" is meant an agent that is administered to a subject in order to reduce one or more symptoms of inflammation including: pain, heat, redness, swelling, bradykinin levels, lysosome enzyme levels, histamine levels, interferon-γ levels, IL-8 levels, leukotriene B4 levels, prostaglandin levels, TNF-α levels, and IL-1 levels, reduce the migration of inflammatory cells into a tissue, and reduce the number of inflammatory cells present in a tissue. Non-limiting examples of anti-inflammatory agents include non-steroidal anti-inflammatory agents (NSAIDS) (e.g., aspirin, diflusinal, salsalate, ibuprofen, naproxen, fenoprofen, ketoprofen, dexketoprofen, flurbiprofen, oxaprozin, loxoprofen, indomethacin, sulindac, etodolac, ketorolac, diclofenac, nabumetone, piroxicam, meloxicam, tenoxicam, droxicam, lornoxicam, isoxicam, mefanamic acid, meclofenamic acid, flufenamic acid, tolfenamic acid, celecoxib, rofecoxib, valdecoxib, parecoxib, lumiracoxib, etoricoxib, firocoxib, nimesulide, and licofelone), steroids (e.g., hydrocortisone, cortisone, prednisone, prednisolone, methylprednisolone, dexamethasone, betamethasone, triamcinolone, beclometasone, fludrocortisone, deoxycorticosterone, and aldosterone) and calcineurin inhibitors (e.g., cyclosporin, tacrolimus, and sirolimus).

By the term "subject" is meant any mammal (e.g., a human, cow, sheep, horse, cat, dog, goat, and rabbit) or bird (e.g., chicken or turkey).

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows the structure of exemplary TarO inhibitors.

FIG. 8A is a photograph of a checkerboard assay showing the effect of combinations of tunicamycin and Congo Red on the wild type *S. aureus* strain Newman following 20 hours incubation at 37° C. The line delineates the boundary between growth (right side of line) and no growth (left side of line). At sublethal concentrations of Congo Red (1 to 64 mg/L), sublethal concentrations of tunicamycin inhibits bacterial growth.

FIG. 8B is a graph showing the growth of *S. aureus* strain Newman in TSB containing 1 mg/L tunicamycin with (open squares) or without (closed squares) the addition of 10 mg/L Congo Red (arrow) at 2 hours.

FIG. 8C is a graph showing the growth of *S. aureus* strain Newman in TSB containing 10 mg/L Congo Red with (open squares) or without (closed squares) the addition of 1 mg/L tunicamycin (arrow) at 2 hours. In pairwise comparison log rank tests, the difference in survival curves between mock and treatment was $p<0.01$.

FIG. 9B is a graph showing the toxicity of 3.1 mg/L to 50.0 mg/L Congo Red for *C. elegans* (n=40 per well). In pairwise comparison log rank tests, the difference in survival curves between mock and each treatment was $p<0.01$.

DETAILED DESCRIPTION OF THE INVENTION

Figure 1:
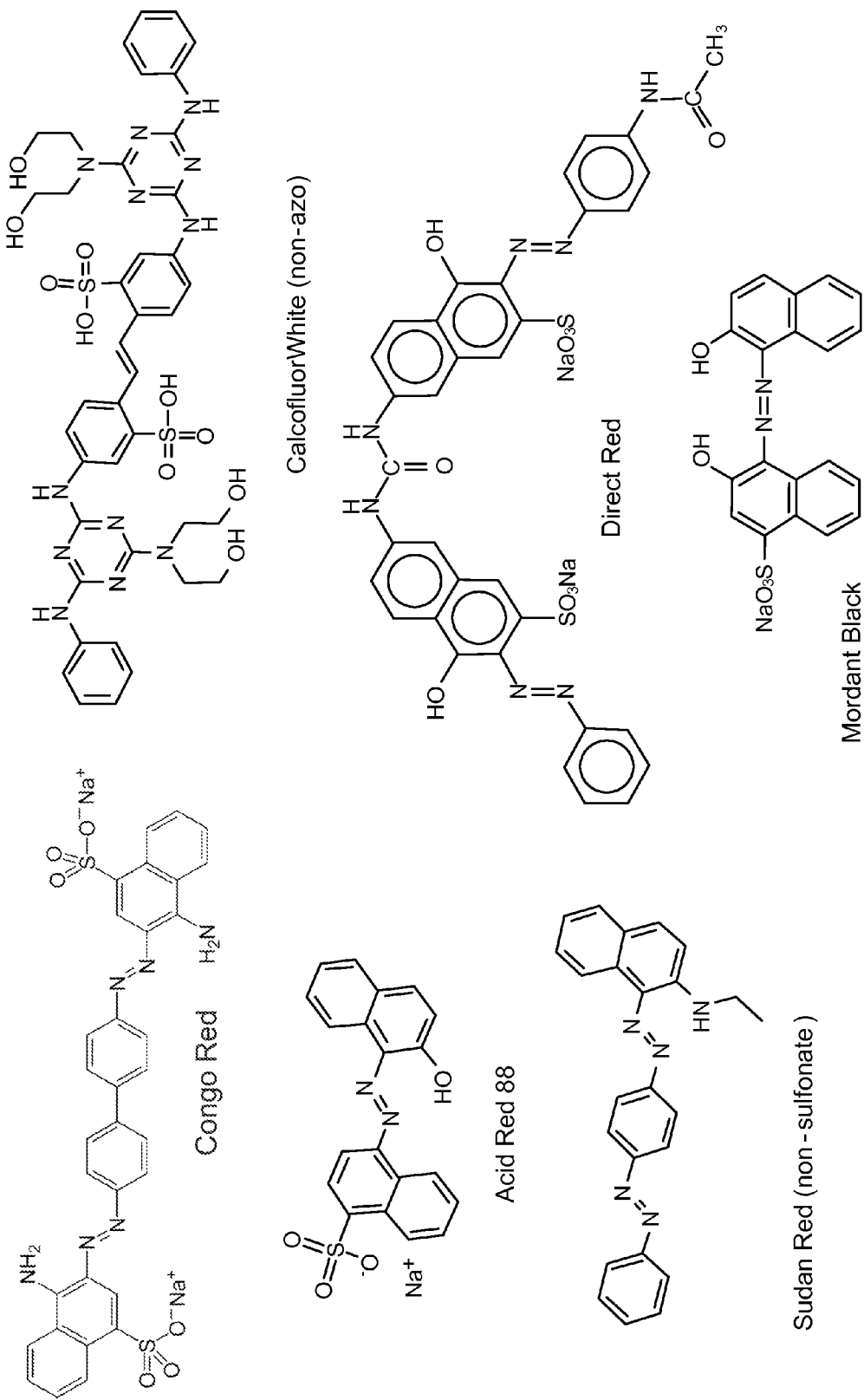
FIG. 1 shows the structure of exemplary dyes, including several azo dyes and anionic azo dyes.

The invention is based, in part, on the discovery that the combination of a dye (e.g., an azo dye, such as an anionic azo dye) and a TarO inhibitor (e.g., a tunicamycin) results in a significant decrease in the proliferation of gram positive bacteria. Thus, provided herein are methods for inducing cell death in a gram positive bacterium and methods for reducing the proliferation of a gram positive bacterium that include contacting a gram positive bacterium with a dye (e.g., an azo dye, such as an anionic azo dye) and a TarO inhibitor. Also provided are methods of treating a subject having a gram positive bacterial infection that include administering to a subject having a gram positive bacterial infection a dye (e.g., an azo dye, such as an anionic azo dye) and a TarO inhibitor (e.g., a tunicamycin or a tunicamycin derivative). Also provided are compositions containing a dye (e.g., an azo dye, such as an anionic azo dye) and a TarO inhibitor (e.g., a tunicamycin or a tunicamycin derivative), and kits containing at least one of these compositions. Various, non-limiting features of each aspect of the invention are described below.

Gram Positive Bacteria

A gram positive bacterium contains teichoic acid (e.g., lipoteichoic acid and/or wall teichoic acid) or a functionally equivalent glycopolymer (e.g., a rhamnopolysaccharide, teichuronic acid, arabinogalactan, lipomannan, and lipoarabinomannan) in its cell wall. In some embodiments, a gram positive bacterium is identified using the Gram staining method (e.g., generally including the steps of staining with crystal violet, treating with an iodine solution, decolorizing with alcohol, and counterstaining with safranine, wherein a gram positive bacterium retains the violet stain). In some embodiments, a gram positive bacterium is identified by detecting the expression of a nucleic acid (e.g., mRNA) specific to a particular gram positive bacterium (e.g., using methods of that utilize polymerase chain reaction (PCR) and primers known in the art). Additional methods for identifying or detecting a gram positive bacterium are known in the art. The presence of a gram positive bacterium or the identity of a gram positive bacterium (genus and/or species) can be determined by a medical worker or a laboratory technician.

In some embodiments, the gram positive bacterium is a *coccus* gram positive bacterium (e.g., a bacterium from the *Streptococcus*, *Enterococcus*, or *Staphylococcus* genus). In some embodiments, the gram positive bacterium is *Staphylococcus aureus* (e.g., a methicillin-resistant *Staphylococcus aureus*). In some embodiments, the gram positive bacterium is a *bacillus* gram positive bacterium (e.g., a gram positive bacterium from the *Cornebacterium*, *Listeria*, *Bacillus*, or *Clostridium* genus). In some embodiments, the gram positive bacterium is *Streptococcus pneumoniae*, *Staphylococcus epidermidis*, *Enterococcus faecalis*, and *Enterococcus*

*faecium*. The specific gram positive bacteria described herein are not limiting. Additional examples of gram positive bacteria are known in the art.

In some embodiments, the gram positive bacterium is an antibiotic-resistant gram positive bacterium (e.g., increased resistance to one or more of a β-lactam antibiotic (e.g., penicillin), vancomycin, a cephalosporin (e.g., cefotaxime or ceftriaxone), and methicillin). In some embodiments, the gram positive bacterium is methicillin-resistant *S. aureus*, a vancomycin-resistant *Enterococcus*, vancomycin-intermediate *S. aureus*, vancomycin-resistant *S. aureus*, vancomycin-tolerant *S. pneumoniae*, β-lactam resistant *Staphylococcus*, penicillin-resistant *E. faecium*, penicillin-resistant *S. pneumoniae*, cephalosporin-resistant *S. pneumoniae*, macrolide-resistant *S. pneumoniae*, streptogramin-resistant *S. pneumoniae*, clindamycin-resistant *S. pneumoniae*, fluoroquinolone-resistant *S. pneumoniae*, rifampin-resistant *S. pneumoniae*, tetracycline-resistant *S. pneumoniae*, choramphenicol-resistant *S. pneumoniae*, β-lactam resistant *Staphylococcus*, vancomycin-resistant *Staphylococcus*, fluoroquinolone-resistant *Staphylococcus*, macrolide-resistant *Staphylococcus*, streptogramin-resistant *Staphylococcus*, clindamycin-resistant *Staphylococcus*, rifampin-resistant *Staphylococcus*, mupirocin-resistant *Staphylococcus*, linezolid-resistant *Staphylococcus*, tetracycline-resistant *Staphylococcus*, chloramphenicol-resistant *Staphylococcus*, β-lactam resistant *Enterococcus*, vancomycin-resistant *Enterococcus*, fluoroquinolone-resistant *Enterococcus*, macrolide-resistant *Enterococcus*, rifampin-resistant *Enterococcus*, aminoglycoside-resistant *Enterococcus*, tetracycline-resistant *Enterococcus*, daptomycin-resistant *Staphylococcus*, daptomycin-resistant *Enterococcus*, or chloramphenicol-resistant *Enterococcus*. Additional examples of antibiotic-resistant gram positive bacteria are known in the art. Antibiotic-resistant gram positive bacteria can be identified by culture of a gram positive bacterium in media that contain one or more antibiotics that the gram positive bacterium to which the bacterium is typically sensitive, whereby an antibiotic resistant gram positive bacterium will continue to proliferate (even at a reduced rate of proliferation) in the medium. Additional methods for detecting an antibiotic-resistant gram positive bacterium are known in the art (e.g., use of PCR to identify the presence of one or more known antibiotic-resistance genes in the bacterium).

Gram Positive Bacterial Infections

Gram positive bacterial infections are a group of pathological conditions that are caused or mediated by the presence of a population of gram positive bacteria in a subject. In some embodiments, the population of gram positive bacteria in a subject can contain two or more different types of gram positive bacteria (e.g., gram positive bacteria from at least two different genus and/or species). In some embodiments, the gram positive bacterial infection is a localized infection (e.g., localized to a specific tissue or subset of tissues in a subject). In some embodiments, the gram positive bacterial infection is localized to the skin, throat, digestive tract, eyes, respiratory tract, urinary tract, nervous system, or vagina. In some embodiments, the gram positive bacterial infection is a systemic infection (e.g., not localized to a specific tissue or subset of tissues in a subject). In some embodiments, the gram positive bacterial infection results in bacteremia or sepsis.

The symptoms of a gram positive infection differ depending on the specific population of gram positive bacteria present in the subject and the site (e.g., tissue or tissues in a subject) where the population of gram positive bacteria are localized. Non-limiting examples of general symptoms of a gram positive bacterial infection in a subject include: fever, swelling, pain, and discharge in the affected area. Additional non-limiting symptoms of gram positive bacterial infection include: sore throat, sinus infection, pharyngitis, colored nasal discharge, headaches, nausea, stomach pain and stomach inflammation, dehydration, peptic ulcer and stomach ulcer, indigestion, meningitis, lethargy, fatigue, stiffness in neck and back, shaking, low blood pressure, redness in the eye, watery or itchy eyes, blurred vision, abdominal cramping, vomiting, weakness, sensory loss, chills, difficulty breathing, chest pain, stuffy nose, congestion, increased heartbeat, discomfort, rash, skin discoloration, strong urge to urinate, burning sensation during urination, blood in urine, cloudy urine, strong-smelling urine, black, tarry, or bloody stools, diarrhea, loss of bowel control, swollen lymph nodes, confusion or disorientation, yeast infection, bacterial vaginosis, sepsis, painful acne, and boils. Additional symptoms of gram positive bacterial infections are known in the art. In some embodiments, a medical professional can diagnose a subject as having a gram positive bacterial infection upon assessing or observing one or more symptom(s) of a gram positive bacterial infection in a subject.

In some embodiments, a subject can be diagnosed or identified as having a gram positive bacterial infection by a medical professional (e.g., a physician, a physician's assistant, a nurse, a nurse's assistant, or a laboratory professional). In some embodiments, a medical professional can also diagnose a subject as having a gram positive bacterial infection by detecting the presence or an increased number of gram positive bacteria in a biological sample from the subject (e.g., a sample containing blood, sputum, urine, nasal discharge, spinal fluid, tissue, or serum from a subject). For example, Gram staining can be performed on a sample from a subject or PCR may be performed to determine whether a nucleic acid expressed in a gram positive bacterium is present in the sample. In some embodiments, the presence of a gram positive bacterium in a sample from a subject indicates that the subject has a gram positive bacterial infection. In some embodiments, the presence of an increased level of gram positive bacteria present in a sample from the subject (e.g., as compared to a reference value, a level of gram positive bacteria present in a sample from a healthy subject, or a level of gram positive bacteria present in a sample obtained from the same subject at an earlier time point) indicates that the subject has a gram positive bacterial infection.

In some embodiments, the gram positive bacterial infection is caused by one or more of any of the gram positive bacteria described herein or known in the art. In some embodiments, the gram positive bacterial infection is caused by an antibiotic-resistant gram positive bacterium (e.g., any of the antibiotic-resistant gram positive bacteria described herein or known in the art).

In some embodiments, the gram positive bacterial infection is chronic. In some embodiments, the gram positive bacterial infection is acute. In some embodiments, the gram positive bacterial infection is a nosocomial gram positive bacterial infection.

In some embodiments, a subject has already been diagnosed as having a gram positive bacterial infection (e.g., infection with one or more of any of the gram positive bacteria described herein or known in the art). In some embodiments, the subject may already be receiving a treatment for gram positive bacterial infection. In some embodiments, the subject may be resistant or show little responsiveness to a previous treatment for a gram positive bacterial infection. In some embodiments, the subject can be an infant, a child, or an adult (e.g., at least 18, 20, 25, 30, 35, 40, 45, 50, 55, 60, 65, 70, 75, 80, 85, or 90 years old). In some embodiments, the subject is a female. In some embodiments, the subject is a male.

Dyes

Dyes represent a class of organic molecules that contain two or more conjugated carbon-carbon double bonds in a linear and/or ring arrangement, and absorb light at a specific wavelength (i.e., absorption wavelength, e.g., a visible wavelength or an ultraviolet wavelength) and transmits or emits light of a different wavelength (i.e., emission wavelength). In some embodiments, the dye absorbs light at a visible wavelength (e.g., an absorption wavelength between 390 nm to 750 nm) and transmits the remaining wavelengths, which are detected visually or instrumentally as a change from white to color. In some embodiments, the dye absorbs light at a visible or ultraviolet wavelength (e.g., an absorption wavelength between 10 nm and 400 nm) and emits light at a different wavelength, resulting in fluorescence. In some embodiments, the dye is a natural dye. In some embodiments, the dye is a synthetic dye.

Non-limiting examples of dyes are shown in FIG. 1. Non-limiting examples of these compounds are dyes used in the food industry (e.g., Food Drug and Cosmetic Act (FD&C) Red dye #40 and FD&C Blue #1), in the cosmetics or pharmaceutical industry, and in the textile industry.

In some embodiments, a dye is an azo-containing dye (R—N=N—R'), such as Congo Red. In some embodiments, the dye lacks an azo bond but contains a conjugated carbon-carbon bond systems (e.g., including two or more (e.g., three, four, five, or six) carbon-carbon double bonds) (e.g., Calcofluor White) that contribute to their spectral and fluorescent properties. In some embodiments, the conjugated carbon-carbon bond system includes an aryl ring. In some embodiments, the conjugated carbon-carbon bond system includes a linear and/or branched carbon chain that contains two or more carbon-carbon double bonds.

Azo Dyes

Azo dyes are compounds include the functional group R—N=N—R', in which R and R' can be, e.g., aryl or alkyl groups. Non-limiting exemplary examples of azo dyes are shown in FIG. 1 (e.g., Congo Red, Acid Red 88, Sudan Red, Direct Red, and Mordant Black). Additional examples of azo dyes are described in Moller et al., *Mutat. Res.* 462:13-30, 2000; Horlein, *Proc. Royal Soc. Med.* 29:313-324, 1936; Domagk, *Deutsche Med. Wochschr.* 61; 250-253, 1935; and Klee et al., *Deut. Med. Wochschr.* 61:253-355, 1935.

In some embodiments, the azo dye has a net negative charge at a neutral or physiological pH (an anionic azo dye). In some embodiments, the anionic azo dye contains at least one (e.g., two, three, four, or five) sulfonic acid groups or a carboxylic acid groups. In some embodiments, the anionic azo dye has the ability to bind to amyloid in biological specimens.

In some embodiments, the azo dye is Congo Red. In some embodiments, the azo dye is Acid Red 88, Sudan Red (non-sulfonate), Direct Red, or Mordant Black. Additional non-limiting examples of azo dyes include: Acid Orange 7, Alizarine Yellow R, Allura Red AC, Amaranth, Amido Black 10B, Aniline Yellow, Azo Violet, Azorubine, Biebrich Scarlet, Bismark Brown R, Bismark Brown Y, Black 7984, Brilliant Black BN, Brown FK, Brown HT, Chrysoine resorcinol, Citrus Red 2, D&C Red 33, Direct Blue 1, Disperse Orange 1, Eriochrome Black T, Evans blue, Fast Yellow AB, Hydroxynaphthol Blue, Janus Green B, Lithol Rubine BK, Methyl Orange, Methyl Red, Methyl Yellow, Mordant Brown 33, Mordant Red 19, Oil Red O, Oil Yellow DE, Orange B, Orange G, Orange GGN, Para Red, Ponceau 2R, Ponceau 4R, Ponceau 6R, Ponceau S, Red 2G, Red No. 40, Scarlet GN, Solvent Red 164, Solvent Red 26, Solvent Yellow 124, Sudan Black B, Sudan I, Sudan II, Sudan III, Sudan IV, Sudan Red 7B, Sudan Red G, Sudan Yellow 3G, Sunset Yellow FCF, Tartrazine, Tropaeolin OO, Trypan Blue, and Yellow 2G. Additional examples of azo dyes are known in the art.

TarO Inhibitors

Tar (teichoic acid ribitol) O is an enzyme involved in the first steps in biosynthesis of *S. aureus* wall teichoic acid. TarO mediates the addition of an activated sugar to the bactroprenol carrier. Non-limiting examples of functional homologues of TarO include enterococcal polysaccharide antigen (Epa) A proteins from *E. faecalis* or *E. faecium* (e.g., described in Palmer et al., *mBio* 3:e00318-11, 2012).

Non-limiting assays for measuring the activity of TarO or a TarO homologue in a cell are described herein and are known in the art. In some embodiments, a TarO inhibitor can be identified as a substance that results in synergistic decrease of gram positive bacteria proliferation in the presence of an azo dye. Additional examples of methods for assessing TarO activity or TarO homologue activity are described in Swoboda et al. (*ChemBioChem*. 11:35-45, 2010), Price et al. (*J. Antibiot.* 60:485, 2007), Swoboda et al. (*ACS Chem. Biol.* 4:875-883, 2009), Meredith et al. (*J. Bacteriol.* 190:3046-3056, 2008), and Hancock et al. (*FEBS Lett.* 69:75-80, 1976). Additional assays for identifying a TarO inhibitor are known in the art.

Non-limiting examples of TarO inhibitors are tunicamycin and tunicamycin derivatives. Tunicamycin is a molecule that contains the following common building blocks: uracil, N-acetyl glycosamine, an 11-carbon aminodialdose (tunicamine), and a fatty acid linked to the amino group. Tunicamycins are produced by strains of *Streptomyces* (e.g., *Streptomyces griseus*; ATCC 31591). There are at least 10 homologs (e.g., tunicamycin A, B, C, and D) (*Dictionary of Antibiotics* 1:714, 1998). The different homologs differ in their fatty acid components, which can vary in chain length (*Dictionary of Antibiotics* 1:714, 1998; Takatsuki et al., *J. Antibiot.* 24:215-223, 1971; Mahoney et al., *J. Chromatography* 198:506-510, 1980; Ito et al., *Argric. Biol. Chem.* 44:695, 1980; Duksin et al., *J. Biol. Chem.* 257:3105-3109, 1982). Several commercially available forms of tunicamycin are a combination of different tunicamycins (e.g., a combination of tunicamycin A, B, C, and D, e.g. T7765 tunicamycin from Sigma Aldrich). In some embodiments of any of the methods described herein, the TarO inhibitor used can be a mixture of one or more tunicamycins (e.g., a combination of tunicamycin A, B, C, and D). Non-limiting exemplary tunicamycins are shown in FIG. 2. Additional examples of tunicamycins are described in Duksin et al. (*J. Biol. Chem.* 257:3105-3109, 1982), Price et al. (*J. Antibiot.* 60(8):485-491, 2007), and U.S. Pat. No. 4,336,333 (herein incorporated by reference in its entirety). Additional examples of tunicamycins known in the art. Exemplary methods for making tunicamycins are described in U.S. Pat. Nos. 4,336, 333 and 4,330,624 (herein incorporated by reference in its entirety).

Non-limiting examples of tunicamycin derivatives are described in Japanese Patent No. 610509955 and Kenig et al. (*J. Antibiot.* (Tokyo) 32:549-554, 1979). In some embodiments, tunicamycin derivatives can contain different lengths of the fatty acyl group (Rn shown in FIG. 2), different hydrophobic moieties in the place of the fatty acyl group (Rn shown in FIG. 2), and/or may contain one or more modifications (added R groups, e.g., substitution of a hydroxyl group with another chemical moiety, e.g., phosphate, a sulfate, a hydrogen, or an alkyl group) to one or both of the sugar moieties in tunicamycin (shown in FIG. 2). Additional examples of tunicamycin derivatives are known in the art. Exemplary methods for testing the ability of a tunicamycin derivative to inhibit TarO activity are described above. Additional methods for testing the ability of a tunicamycin derivative to inhibit TarO activity are known in the art.

Methods of Inducing Cell Death or Reducing Proliferation in a Gram Positive Bacterium Also provided herein are methods of inducing cell death in a gram positive bacterium. These methods include contacting a gram positive bacterium with at least one dye (e.g., any of the azo dyes, such as an anionic azo dye, described herein or known in the art) and at least one TarO inhibitor (e.g., any of the TarO inhibitors described herein or known in the art).

Also provided herein are methods of reducing proliferation of a gram positive bacterium. These methods include contacting a gram positive bacterium with at least one dye (e.g., any of the azo dyes, such as an anionic azo dye, described herein or known in the art) and at least one TarO inhibitor (e.g., any of the TarO inhibitors described herein or known in the art).

In some embodiments, the gram positive bacterium is in vitro. In some embodiments, the gram positive bacterium is present in a cell culture (e.g., a liquid, semi-solid, or solid culture medium) (e.g., a plant cell culture medium, a yeast cell culture medium, a mammalian cell culture medium, or a bacterial cell culture medium). In some embodiments, the gram positive bacterium is present in a storage medium (e.g., a liquid, solid, or solid storage medium) (e.g., a medium that is used to store any composition for a period of time, e.g., a composition of mammalian cells).

In some embodiments, the gram positive bacterium is present in or on a food composition (or an ingredient thereof) (e.g., a liquid, solid, or semi-solid composition). In some embodiments, the gram positive bacterium is present in a veterinary feed composition.

In some embodiments, the gram positive bacterium is present in a pharmaceutical composition (e.g., a composition containing at least one pharmaceutically active agent, e.g., in addition to a dye (e.g., an azo dye, such as an anionic azo dye and a TarO inhibitor) (e.g., a liquid, solid, or semi-solid pharmaceutical composition). In some embodiments, the gram positive bacterium is present in a cosmetic composition (e.g., a cream, lotion, ointment, solution, shampoo, spray, powder, or gel). In some embodiments, the gram positive bacterium is present in a wound in a subject (e.g., a cut, burn, abrasion, puncture, or surgical incision). In some embodiments, the gram positive bacterium is present in or on the skin, on the eye, in the lung, in the throat, or in the mouth of a subject. In some embodiments, the gram positive bacterium is present in a household item or on a household surface (e.g., any of the household surfaces described herein or known in the art). In some embodiments, the gram positive bacterium is present in or on equipment or an instrument used in a medical procedure (e.g., any of the exemplary medical procedures described herein or known in the art).

In some embodiments, a composition is first identified as containing a gram positive bacterium, and selected for use in the methods described herein. In some embodiments, a composition is not previously identified as containing a gram positive bacterium prior to its use in the methods described herein.

In some embodiments, the gram positive bacterium is present in a mammal (e.g., a human, pig, dog, cat, horse, sheep, cow, llama, or goat). In some embodiments, the gram positive bacterium is present in a bird (e.g., a chicken or turkey). In some embodiments, the subject has already been diagnosed or identified as having a gram positive bacterial infection (e.g., any of the gram positive bacterial infections described herein). In some embodiments, the subject may already have be receiving treatment for a gram positive bacterial infection.

In some embodiments, the gram positive bacterium is any of the gram positive bacteria described herein. In some embodiments, the gram positive bacterium is a *coccus* gram positive bacterium (e.g., a gram positive bacterium from the *Streptococcus*, *Enterococcus*, or *Staphylococcus* genus). In some embodiments, the gram positive bacterium is *Staphylococcus aureus* (e.g., methicillin-resistant *Staphylococcus aureus*). In some embodiments, the gram positive bacterium is a *bacillus* gram positive bacterium (e.g., a gram positive bacterium from the *Cornebacterium*, *Listeria*, *Bacillus*, or *Clostridium* genus). Additional examples of gram positive bacteria are known in the art. In some embodiments, the gram positive bacterium is an antibiotic-resistant gram positive bacterium (e.g., any of the antibiotic-resistant gram positive bacterium described herein or known in the art).

In some embodiments, a dye (e.g., an azo dye, such as an anionic azo dye) and an TarO inhibitor (e.g., an tunicamycin or tunicamycin derivative) are formulated in a single composition (e.g., a solid, semi-solid, spray, or liquid).

In some embodiments, cell death or proliferation of a gram positive bacterium can be detected using microscopic techniques (e.g., transmission electron microscopy or oil-immersion microscopy). In some embodiments, cell death of a gram positive bacterium can be observed, e.g., by the disruption of the cell wall. In some embodiments, the proliferation of a gram positive bacterium can be detected through the use of a hemocytometer with a microscopic method. In some embodiments, proliferation can be determined by assessing the number of gram positive bacteria in a sample (e.g., at more than one time point or continuously over time). In some embodiments, proliferation is detected as an increase in the number of gram positive bacterial in a sample (e.g., a biological sample) collected at a second time point compared to the number of gram positive bacteria present in a sample (e.g., a biological sample) at a first time point). In some embodiments, cell death of a gram positive bacterium can be indirectly detected by a decrease in the proliferation of the gram positive bacterium (e.g., detected using any of the methods described herein) (e.g., relative to the proliferation of a gram positive bacterium not treated with a dye (e.g., an azo dye, such as an anionic azo dye) and a TarO inhibitor (e.g., an tunicmycin or a tunicamycin derivative). In some embodiments, proliferation of a gram positive bacterium in a liquid composition (e.g., a liquid culture medium) can be detected by measuring the light absorbance of the culture (e.g., 600 nm) (e.g., the rate of the increase in the light absorbance of the culture over time or an increase in the light absorbance of the culture at a second time point compared to an earlier time point indicates proliferation). In some embodiments, cell death of a gram positive bacterium or a decrease in the proliferation of a gram positive bacterium in a subject can be indirectly detected by a decrease in the number of symptoms of a gram positive bacterial infection in a subject or a decrease in the severity, duration, and/or frequency of one or more symptoms of a gram positive bacterial infection in a subject (e.g., any of the symptoms of a gram positive bacterial infection described herein).

Methods of Treating Gram Positive Bacterial Infections

Also provided herein are methods of treating a subject having a gram positive bacterial infection. These methods include administering to the subject at least one dye (e.g., at least one azo dye described herein or known in the art, e.g., an anionic azo dye) and at least one TarO inhibitor (e.g., at least one of any of the tunicamycins or tunicamycin derivatives described herein or known in the art). In some embodiments, the gram positive bacterial infection is one of the gram positive bacterial infections described herein. Additional examples of gram positive bacterial infections are known in the art.

In some embodiments, the gram positive bacterial infection is caused by a *coccus* gram positive bacterium (e.g., a gram positive bacterium from the *Streptococcus, Enterococcus*, or *Staphylococcus* genus). In some embodiments, the gram positive bacterial infection is caused by *Staphylococcus aureus* (e.g., methicillin-resistant *Staphylococcus aureus*). In some embodiments, the gram positive bacterial infection is caused by a *bacillus* gram positive bacterium (e.g., a gram positive bacterium from the *Cornebacterium, Listeria, Bacillus*, or *Clostridium* genus). In some embodiments, the gram positive bacterial infection is caused by an antibiotic-resistant gram positive bacterium (e.g., any of the antibiotic-resistant gram positive bacteria described herein or known in the art).

In some embodiments, the population of gram positive bacteria in a subject can contain two or more different types of gram positive bacteria (e.g., gram positive bacteria from at least two different genus and/or species). In some embodiments, the gram positive bacterial infection is caused by an antibiotic-resistant gram positive bacterium (e.g., any of the antibiotic-resistant gram positive bacteria described herein).

In some embodiments, the gram positive bacterial infection is chronic. In some embodiments, the gram positive bacterial infection is acute. In some embodiments, the gram positive bacterial infection is a nosocomial gram positive bacterial infection.

In some embodiments, a subject has already been diagnosed as having a gram positive bacterial infection (e.g., infection with one or more of any of the gram positive bacteria described herein or known in the art). In some embodiments, the subject may already be receiving a treatment for gram positive bacterial infection. In some embodiments, the subject may be resistant or show little responsiveness to a previous treatment for a gram positive bacterial infection. In some embodiments, the subject can be an infant, a child, or an adult (e.g., at least 18, 20, 25, 30, 35, 40, 45, 50, 55, 60, 65, 70, 75, 80, 85, or 90 years old). In some embodiments, the subject is a female. In some embodiments, the subject is a male.

Some embodiments further include selecting a subject having a gram positive bacterial infection or suspected of having a gram positive bacterial infection (e.g., an antibiotic-resistant gram positive bacterial infection). Some embodiments include selecting a subject at risk of developing a gram positive bacterial infection (e.g., an antibiotic-resistant gram positive bacterial infection).

In some embodiments, the gram positive bacterial infection is a localized infection (e.g., localized to a specific tissue or set of tissues in a subject). In some embodiments, the gram positive bacterial infection is localized to the skin, throat, digestive tract, eyes, respiratory tract, urinary tract, nervous system, or vagina. In some embodiments, the gram positive bacterial infection is a systemic infection (e.g., not localized to a specific tissue or set of tissues in a subject). In some embodiments, the gram positive bacterial infection results in sepsis.

Successful treatment of a gram positive bacterial infection in a subject can be detected by the observance or detection of a decrease in the number of symptoms of a gram positive bacterial infection in a subject (e.g., any of the symptoms of a gram positive bacterial infection described herein or known in the art) or a reduction in the duration, severity, or frequency of one or more (e.g., at least two, three, or four) symptoms of a gram positive bacterial infection (e.g., any of the symptoms of a gram positive bacterial infection described herein or known in the art). In some embodiments, a treatment of a gram positive bacterial infection can be assessed by physical examination of the subject. In some embodiments, successful treatment of a gram positive bacterial infection can be assessed by a medical professional (e.g., a physician, a physician's assistant, a nurse, a nurse's assistant, or a technician).

In some embodiments, the TarO inhibitor is a tunicamycin or a tunicamycin derivative (e.g., any of the tunicamycins or tunicamycin derivatives described herein or known in the art). In some embodiments, the dye is an azo dye (e.g., any of the azo dyes described herein or known in the art, e.g., an anionic azo dye). In some embodiments, the dye is an azo dye selected from the group of Congo Red, Sudan Red, Direct Red, Mordant black, and Acid Red 88. In some embodiments, the dye is Congo Red and the TarO inhibitor is a tunicamycin.

In some embodiments, the dye (e.g., azo dye, such as an anionic azo dye) and/or TarO inhibitor is formulated for oral, nasal, intravenous, intraarterial, topical, optical, subcutaneous, intramuscular, or intraperitoneal administration. In some embodiments, the dye (e.g., azo dye, such as an anionic azo dye) and/or TarO inhibitor are administered by oral, intravenous, intraarterial, nasal, topical, optical, subcutaneous, intramuscular, or intraperitoneal administration.

In some embodiments, the dye (e.g., azo dye, such as an anionic azo dye) and TarO inhibitor are formulated in a single composition (e.g., formulated for oral, intravenous, intraarterial, nasal, topical, optical, subcutaneous, intramuscular, or intraperitoneal administration). In some embodiments, the dye (e.g., azo dye, such as an anionic azo dye) and TarO inhibitor are formulated in a single composition for oral administration. In some embodiments, the single composition containing a dye (e.g., azo dye, such as an anionic azo dye) and TarO inhibitor are administered by oral, intravenous, intaarterial, nasal, topical, optical, subcutaneous, intramuscular, or intraperitoneal administration.

The amount of dye (e.g., azo dye, such as an anionic azo dye) and TarO inhibitor administered to a subject can be an amount that results in a significant, detectable, or observable amount of cell death in gram positive bacteria, an amount that results in a significant, detectable, or observable decrease in the proliferation of gram positive bacteria, an amount that results in a decrease in the number of symptoms of a gram positive bacterial infection in a subject (e.g., any of the symptoms of a gram positive bacterial infection described herein), an amount that results in a decrease in the severity, frequency, or duration of one or more symptoms of a gram positive bacterial infection in a subject (e.g., any of the symptoms of a gram positive bacterial infection described herein), or an amount that results in reduced titer of gram positive bacterial cells in a sample (e.g., a biological sample from a subject) (e.g., as compared to a sample from a subject having a gram positive bacterial infection that is not treated with a dye (e.g., an azo dye, such as an anionic azo dye) and a TarO inhibitor, or a biological sample from the same subject at an earlier time point (e.g., a time point before treatment or an earlier time point during treatment). A medical professional can determine the appropriate dosage of a dye (e.g., an azo dye) and a TarO inhibitor to administer to the subject based on a number of factors (e.g., the tissue affected by the gram positive bacterial infection, the specific gram positive bacteria causing the infection, the subject's age, general health, sex, and body weight). Exemplary dosages of dye (e.g., an azo dye, such as an anionic azo dye) and a TarO inhibitor to be administered to a subject are described herein.

In some embodiments, the dye (e.g., azo dye, such as an anionic azo dye) and/or TarO inhibitor are formulated in a physiologically acceptable excipient or buffer. In some embodiments, the dye (e.g., azo dye, such as an anionic azo dye) and the TarO inhibitor can be administered in separate compositions (e.g., by the same (e.g., oral administration) or different routes of administration (e.g., any combination of the various routes of administration described herein, e.g., one composition administered by oral administration and one composition administered by subcutaneous)).

In some embodiments, the dye (e.g., an azo dye, such as an anionic azo dye) and/or the TarO inhibitor are administered to the subject at least once every two months (e.g., at least once every month, at least once every two weeks, at least once a week, or at least once, twice, or three times a day). In some embodiments, the subject can be periodically administered a dye (e.g., an azo dye, such as an anionic azo dye) and a TarO inhibitor over a period of at least two days (e.g., at least one week, at least one month, two months, six months, one year, and two years).

Some embodiments further include administering to the subject one or more additional agents (e.g., an additional antibiotic, anti-parasitic agent, an anti-viral agent, an anti-fungal agent, and an anti-inflammatory agent). Non-limiting examples of additional antibiotics, anti-parasitic agents, anti-fungal agents, anti-viral agents, and anti-inflammatory agents that can also be administered to a subject in any of the present methods are described herein. In some embodiments, the one or more additional agents are present in the same formulation with a dye (e.g., an azo dye, such as an anionic azo dye) and/or a TarO inhibitor.

In some embodiments, the subject is a mammal (e.g., any of the mammals described herein, e.g., a human). In some embodiments, the subject is a bird (e.g., a turkey or chicken).

In some embodiments, the subject is a human child, teenager, or adult (e.g., at least 18, 20, 25, 30, 35, 40, 45, 50, 55, 60, 65, 70, 75, 80, 85, or 90 years old). In some embodiments, the subject is a human female. In some embodiments, the subject is a human male.

Compositions

Also provided are compositions containing one or more (e.g., at least two, three, four, or five) dyes (e.g., any of the azo dyes, e.g., anionic azo dyes, described herein or known in the art) and one or more TarO inhibitors (e.g., any of the TarO inhibitors described herein or known in the art). In some embodiments, the compositions contain one or more pharmaceutically acceptable excipients or buffers. In some embodiments, the compositions are formulated as a solid (e.g., a pill or capsule for oral administration). In some embodiments, the compositions are formulated as a liquid or gel. In some embodiments, the compositions are formulated for ocular administration (e.g., eye drop formulations). In some embodiments, the compositions are formulated for systemic administration (e.g., for oral, intravenous, intraarterial, intramuscular, intraperitoneal, or subcutaneous administration). In some embodiments, the compositions are formulated as a slow-release formulation.

Pharmaceutical compositions are formulated to be compatible with their intended route of administration or the type of infection, e.g., systemic or local infection. In some embodiments, the compositions are formulated for oral, intravenous, intradermal, subcutaneous, transmucosal (e.g., nasal sprays are formulated for inhalation), or transdermal (e.g., topical ointments, salves, gels, patches or creams as generally known in the art) administration. The compositions can include a sterile diluent (e.g., sterile water or saline), a fixed oil, polyethylene glycol, glycerine, propylene glycol, or other synthetic solvents; additional antibacterial or antifungal agents, such as benzyl alcohol or methyl parabens, chlorobutanol, phenol, ascorbic acid, thimerosal, and the like; antioxidants, such as ascorbic acid or sodium bisulfite; chelating agents, such as ethylenediaminetetraacetic acid; buffers such as acetates, citrates, or phosphates; and isotonic agents, such as sugars (e.g., dextrose), polyalcohols (e.g., manitol or sorbitol), or salts (e.g., sodium chloride). Liposomal suspensions can also be used as pharmaceutically acceptable carriers (see, e.g., U.S. Pat. No. 4,522,811). Preparations of the compositions can be formulated and enclosed in ampules, disposable syringes, a pump dispenser, a spray bottle, or multiple dose vials. Where required (as in, for example, injectable formulations), proper fluidity can be maintained by, for example, the use of a coating such as lecithin, or a surfactant. Absorption of the active ingredient can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Where oral administration is intended, the agent can be included in pills, capsules, troches and the like, and can contain any of the following ingredients, or compounds of a similar nature: a binder, such as microcrystalline cellulose, gum tragacanth, or gelatin; an excipient, such as starch or lactose; a disintegrating agent, such as alginic acid, Primogel, or corn starch; a lubricant, such as magnesium stearate; a glidant, such as colloidal silicon dioxide; a sweetening agent, such as sucrose or saccharin; or a flavoring agent, such as peppermint, methyl salicylate, or orange flavoring.

The compositions described herein can be formulated for ocular or parenteral (e.g., oral) administration in dosage unit form (i.e., physically discrete units containing a predetermined quantity of active compound for ease of administration and uniformity of dosage). Toxicity and therapeutic efficacy of compounds can be determined by standard pharmaceutical procedures in cell cultures or experimental animals. One can, for example, determine the LD50 (the dose lethal to 50% of the population) and the ED50 (the dose therapeutically effective in 50% of the population), the therapeutic index being the ratio of LD50:ED50. Agents that exhibit high therapeutic indices are preferred. Where an agent exhibits an undesirable side effect, care should be taken to target that agent to the site of the affected tissue (the aim being to minimize potential damage to unaffected cells and, thereby, reduce side effects). Toxicity and therapeutic efficacy can be determined by other standard pharmaceutical procedures.

In some embodiments, the amount of a dye present (e.g., an azo dye, such as an anionic azo dye) (or each dye when more than one dye is present) in a single dose of the composition is between 1 mg and 50 mg, 5 mg and 100 mg, 10 mg to 100 mg, 20 mg to 50 mg, 50 mg to 100 mg, 75 mg to 150 mg, 100 mg to 200 mg, or 150 mg to 250 mg. In some embodiments, the amount of a TarO inhibitor present (or each TarO inhibitor when more than one TarO inhibitor is present) in a single dose of the composition is between 1 mg and 50 mg, 5 mg and 100 mg, 10 mg to 100 mg, 20 mg to 50 mg, 50 mg to 100 mg, 75 mg to 150 mg, 100 mg to 200 mg, or 150 mg to 250 mg. Some embodiments of the compositions further include one or more additional agents (e.g., one or more (e.g., two, three, four, or five), e.g., agents selected from the group of antibiotics, anti-parasitic agents, anti-viral agents, anti-fungal agents, and anti-inflammatory agents. In some embodiments, the amount of each additional agent in a single dose of the composition is between is between 1 mg and 50 mg, 5 mg and 100 mg, 10 mg to 100 mg, 20 mg to 50 mg, 50 mg to 100 mg, 75 mg to 150 mg, 100 mg to 200 mg, or 150 mg to 250 mg.

Some embodiments of any of the compositions described herein can further contain one or more agents selected from the group of: one or more (e.g., two, three, four, or five) additional antibiotics (e.g., daptomycin, gemifloxacin, telavancin, ceftaroline, fidaxomicin, amikacin, gentamicin, kanamycin, neomycin, netilmicin, paromomycin, streptomycin, tobramycin, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmatazole, cefonicid, cefotetan, cefoxitin, cefrpozil, cefuroxime, cefuzonam, cefcapene, cefdaloxime, cefdinir, cefditoren, cefetamet, cefixime, cefmenozine, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinome, cefaclomezine, cefaloram, cefaparole, cefcanel, cefedrolo, cefempidone, cefetrizole, cefivitril, cefmatilen, cefmepidium, cefovecin, cefoxazole, cefrotil, cefsumide, cefauracetime, ceftioxide, impenem, doripenem, meropenem, ertapenem, flumequine, nalidixic acid, oxolinic acid, piromidic acid, pipemidic acid, rosoxacin, ciprofloxacin, enoxacin, lomefloxacin, nadifloxacin, nadifloxacin, norfloxacin, ofloxacin, perfloxacin, rulfoxacin, balofloxacin, gatifloxacin, grepafloxacin, levofloxacin, moxifloxacin, pazufloxacin, sparfloxacin, temafloxacin, tosulfoxacin, basifloxacin, clinafloxacin, gemifloxacin, sitafloxacin, trovafloxacin, prulifloxacin, azithromycin, erythromycin, clarithromycin, dirithromycin, roxithromycin, telithromycin, amoxicillin, ampicillin, bacampicillin, carbenicillin, cloxacillin, dicloxacillin, flucloxacillin, mezlocillin, nafcillin, oxacillin, penicillin G, penicillin V, piperacillin, pivampicillin, pivmecillinam, pimecillinam, ticarcillin, sulfamethizole, sulfamethoxazole, sulfisoxazole, sulfisoxazole, trimethoprim-sulfamethoxazole, demeclocycline, doxycycline, minocycline, oxytetracycline, tetracycline, tigecycline, vancomycin, metronidazole, tinidazole, nitrofurantoin, chloramphenicol, linezolid, rifampin, rifabutin, rifapentine, clindamycin, linconmycin, pristinamycin, and quinupristin), one or more anti-fungal agents (e.g., amphotericin B, candicidin, filipin, hamycin, natamycin, nystatin, rimocidin, bifonazole, butoconazole, clutrimazole, econazole, fenticonazole, isocanazole, ketoconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenfaine, naftifine, terbinafine, anidulafungin, caspofungin, micafungin, benzoic acid, ciclopirox, flucytosine, griseofulvin, haloprogin, polygodial, tolnaftate, undecylenic acid, and cystal violet), one or more anti-viral agents (e.g., abacavir, aciclovir, acyclovir, adefovir, amantadine, amprenavir, ampligen, arbidol, atazanavir, atripla, boceprevirertet, cidofovir, combivir, darunavir, delaviridine, didanosine, docosanol, edoxudine, efavirenz, emtricitabine, enfuvirtide, entecavir, famciclovir, fomivirsen, fosamprenavir, fascarnet, fosfonet, ganciclovir, ibacitabine, immunovir, idoxuridine, imquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alpha-2a, penciclovir, peramivir, pleconaril, podophyllotoxin, raltegravir, ribavirin, a reverse transcriptase inhibitor, ribavirin, rimantadine, ritonavir, pyramidine, saquinavir, stavudine, telaprevir, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine), one or more anti-parasitic agents (e.g., mebendazole, pyrantel pamoate, thiabendazole, diethylcarbamazine, ivermectin, niclosamide, praziquantel, albendazole, praziquantel, rifampin, amphotericin B, melarsoprol, eflornithine, metronidazole, tinidazole, and miltefosine), and one or more anti-inflammatory agents (e.g., any of the exemplary anti-inflammatory agents described herein or known in the art).

In some embodiments, the composition containing at least one dye (e.g., an azo dye, such as an anionic azo dye) and at least one TarO inhibitor is a food composition (e.g., a liquid or a solid), e.g., where the at least one dye (e.g., an azo dye, such as an anionic azo dye) and at least one TarO inhibitor is present in or on (e.g., layered on the surface) the food composition. Also provided herein are methods of making a food composition that include providing a food composition (or an ingredient of a food composition), and coating the food composition (or an ingredient of a food composition) or adding to the food composition (or an ingredient of a food composition) at least one dye (e.g., an azo dye, such as an anionic azo dye) and at least one TarO inhibitor. In some embodiments, the food composition is a veterinary food composition (e.g., a solid feed or a liquid). In some embodiments, any of the compositions described herein can be a food, beverage, or food or vitamin supplement. For example, a food composition can be a food, beverage, ingredient, food coating, or food or vitamin supplement for humans, or domestic animals or birds (e.g., an agricultural feed for chickens, turkeys, cows, pigs, horses, geese, goats, and sheep). In some embodiments, the food compositions described herein can be packaged and stored for a substantial period of time (e.g., at least one week, two week, three weeks, four weeks, five weeks, six weeks, seven weeks, or eight weeks).

In some embodiments, the composition containing at least one dye (e.g., an azo dye, such as an anionic azo dye) and at least TarO inhibitor is a pharmaceutical composition (e.g., a pharmaceutical composition containing at least one additional pharmaceutical agent that is formulated using any of the methods described herein or known in the art) or a cosmetic composition (e.g., a cream, lotion, gel, ointment, spray, shampoo, powder, or liquid composition). Also provided herein are methods of making a pharmaceutical or cosmetic composition that include providing a pharmaceutical or cosmetic composition (or an ingredient thereof) and coating or adding to the pharmaceutical or cosmetic composition (or an ingredient thereof) at least one dye (e.g., an azo dye, such as an anionic azo dye) and at least one TarO inhibitor. Non-limiting examples of cosmetic compositions provided herein include make-up (e.g., a liquid, powder, spray, or lotion), shampoo, conditioner, hair treatments (e.g., gel, lotion, liquid, spray, or powder), or topical skin treatments or injections (e.g., gel, lotion, liquid, spray, or power).

In some embodiments, any of the compositions described herein can be a household cleaning product (e.g., a liquid, gel, solid, or spray). For example, a household cleaning product can be a general purpose cleaner, a disinfectant, a scouring cleanser, a glass cleaner, a carpet/upholstery cleaner, a floor cleaner, a toilet bowl cleaner, a bathroom cleaner, a sink cleaner, a kitchen cleaner, a spot or stain remover, or a dusting spray or polish). Some embodiments of these compositions further include one or more additional agents selected from the group consisting of fragrances, one or more surfactants (e.g., linear alkylbenzene sulfonate, nonylphenol ethoxylate, alcohol sulfates, soap, cocamide diethanolamine, and alkylpolyglucosides), one or more solvents (e.g., pine oil, d-limonene, ethylene glycol mono-n-butyl ether, and other glycol ethers), one or more additional antimicrobial agents (e.g., quarternary ammonium compounds), one or more binders (e.g., ethylenediaminetetraacetic acid (EDTA), sodium carbonate, sodium bicarbonate, sodium phosphates, and sodium metasilicate), and one or more organic ingredients (e.g., fats, oils, petroleum-based intermediates, ammonia, chlorine, or sodium hydroxide).

In some embodiments, any of the compositions described herein can be detergents or soaps (e.g., laundry detergent and hand soap). In some embodiments, the detergents and soaps can also contain one or more ingredients selected from the group consisting of: one or more surfactants (e.g., any of the exemplary surfactants described herein or known in the art), one or more binders (e.g., any of the exemplary surfactants described herein or known in the art), one or more fillers, one or more enzymes (e.g., amylase, protease, and pectinase), one or more dyes, one or more fragrances, disodium diaminostilbene disulfonate, tricolsan, sodium laureth sulfate, ammonium lauryl sulfate, cocamide MEA, glycerin, one or more essential oils, and silicone polyether.

In some embodiments, any of the compositions described herein can be topical sterilizing compositions (e.g., a lotion, liquid, gel, or spray). For example, a composition described herein can be a hand-sanitizing composition (e.g., a gel, a liquid, or a lotion). In some embodiments, a hand-sanitizing composition can further contain one or more additional ingredients selected from the group consisting of: isopropanol, ethanol, n-propanol, povidone-iodine, polyacrylic acid, a humectant (e.g., glycerin), propylene glycol, and an plant essential oil.

In some embodiments, any of the compositions provided herein can be wound (e.g., a cut, burn, abrasion, or surgical incision) sterilization compositions (e.g., a liquid, gel, spray, lotion, or cream) (e.g., a wound irrigation solution). In some embodiments, a wound sterilization composition further contains one or more additional anti-microbial agents (e.g., any of the additional anti-microbial agents described herein or known in the art), one or more anti-fungal agents (e.g., any of the anti-fungal agents described herein or known in the art), one or more anti-parasitic agents (e.g., any of the anti-parasitic agents described herein or known in the art), and/or one or more anti-viral agents (e.g., any of the anti-viral agents described herein or known in the art). In some embodiments, the composition is a bandage, gauze, or suture that is impregnated with any of the wound sterilization compositions or compositions described herein. In some embodiments, a wound sterilization composition (e.g., a liquid, gel, spray, lotion, or solid) can be used to sterilize equipment or instruments used in a medical procedure (e.g., a surgical procedure, a diagnostic procedure, a medical monitoring procedure, or a clinical laboratory test).

In some embodiments, any of the compositions described herein can be a gram positive bacteria staining compositions (e.g., for use in a clinical microbiology lab or to identify surfaces or compositions contaminates with gram positive bacteria). For example, the gram positive staining compositions described herein can be provided in the form of a liquid, gel, tablet, solid, or spray. For example, the gram positive bacteria staining composition can be used to stain gram positive bacteria that are present on the surface of the skin, on teeth, or in the eye of a subject.

In some embodiments, the composition containing at least one dye (e.g., an azo dye, such as an anionic azo dye) and at least one TarO inhibitor is a cell culture medium (e.g., a fungal cell, plant cell, mammalian cell, or bacterial cell culture) (e.g., a solid, liquid, or semi-solid culture medium). Also provided herein are methods of culturing a cell (e.g., a fungal cell, plant cell, mammalian cell, or bacterial cell) that including incubating a cell with a culture medium that contains at least one dye (e.g., an azo dye, such as an anionic azo dye) and at least one TarO inhibitor (e.g., under conditions that sufficient for cell growth). Also provided are methods of making a culture medium that include adding or mixing to a culture medium at least one dye (e.g., an azo dye, such as an anionic azo dye) and at least one TarO inhibitor.

Kits

Also provided herein are kits that contain any of the compositions described herein. In some embodiments, the kits can further include an item for use in administering a composition (e.g., any of the compositions described herein) to the subject (e.g., a syringe, e.g., a pre-filled syringe). In some embodiments, the kits contain one or more doses (e.g., at least two, three, four, five, six, seven, eight, nine, ten, eleven, twelve, thirteen, fourteen, twenty, thirty, or forty doses) (e.g., oral doses) of any of the compositions described herein. In some embodiments, the kit further contains instructions for administering the composition (or a dose of the composition) to a subject having a gram positive bacterial infection. In some embodiments, the kit further contains instructions for performing any of the methods described herein (e.g., any of the methods of treating a subject having a gram positive bacterial infection described herein).

The invention is further described in the following example, which does not limit the scope of the invention described in the claims.

EXAMPLE

Example 1. Combinations of an Azo Dye and a TarO Inhibitor Decrease Proliferation of Gram Positive Bacteria Experiments were performed to study the extent to which teichoic acid contributes to protection from dyes, such as azo dyes, and to identify barriers to drug penetration for development of new antibiotics to treat gram positive bacterial infections.

Materials and Methods

Strains and Growth Conditions.

The bacterial strains used in these experiments are listed in Table 1. *S. aureus* was grown in tryptic soy broth (TSB), and antibiotic resistances were selected with tetracycline (Tc; 2.5 mg/L), and kanamycin (Km; 50 mg/L).

TABLE 1

S. Aureus Strains

| Strain | Genotype and/or phenotype |
|---|---|
| RN6390 | Prophage-cured derivative of NCTC 8325[1] |
| RN4220 | A mutant of NCTC 8325-4 that accepts foreign DNA partial agr defect[2] |
| Newman | Clinical isolates, methicillin susceptible strain[3] |
| MW2 | Clinical isolates, methicillin resistant strain[4] |
| RN6390 ΔtarO | RN6390 ΔtarO::tetL, Tc[r5] |
| RN4220 ΔtarO | RN4220 ΔtarO[6] |
| RN4220 ΔtarA | RN4220 ΔtarA[7] |
| RN4220 ΔtarK | RN4220 ΔtarK[7] |
| RN4220 ΔltaS | RN4200 ΔltaS::phleo/pM101, Km[r8] |
| RN4220 ΔltaS-ltaS | RN4200 ΔltaS::phleo/pM101-ltaS, , Km[r8] |
| Newman ΔtarO | Newman ΔtarO[9] |

[1]Peng et al., *J. Bacteriol.* 170: 4365-4372, 1988.
[2]Kreiswirth et al., *Nature* 305: 709-712, 1983.
[3]Duthie et al., *J. Gen. Microbiol.* 6: 95-107, 1952.
[4]Centers for Disease Control and Prevention, *JAMA* 282: 1123-1125, 1999.
[5]Campbell et al., *ACS Chem. Biol.* 6: 106-116, 2011.
[6]Grundling et al., *J. Bacteriol.* 188: 2463-2472, 2006.
[7]Chang et al., *N. Engl. J. Med.* 348: 1342-1347, 2003.
[8]Oku et al., *J. Bacteriol.* 191: 141-151, 2009.
[9]Grundling et al., *J. Bacteriol.* 188: 2463-2472, 2006.

Congo Red Sensitivity.

Congo Red sensitivity tests were conducted as previously described (Hubscher et al., *FEMS Microbiol. Lett.* 295:251-260, 2009), with minor modification. Briefly, 10-fold dilutions, starting at $10^6$ colony forming units (CFU) in 5 µL, were spotted on brain heart infusion (BHI) agar or Luria-Bertani (LB) agar, supplemented with 0.08% (w/v) Congo Red where appropriate. The Congo Red agar plates were incubated at 37° C. or 30° C. for 24 hours. As a precaution to prevent possible inactivation of Congo Red by light, the plates were incubated in the dark. Sensitivity to Congo Red was determined by comparing colony density between parental and mutant strains on control and Congo Red plates. Sudan Red 7B (0.08% w/v), Calcofluor White (0.01% w/v), Direct Red (0.08% w/v), Mordant Black (0.08% w/v), or Acid Red (0.08% w/v) in BHI agar were tested similarly.

MIC Determination.

In vitro susceptibility tests (minimum inhibitory concentration [MIC]) were conducted using the Clinical and Laboratory Standards Institute (CLSI) broth microplate assay guidelines (Clinical and Laboratory Standards Institute, Performance Standards for Antimicrobial Susceptibility Testing; 16th Informational Supplement, CLSI M100-S16, Wayne, Pa., 2006). Because of temperature sensitivity, to determine susceptibility of RN4220 ΔltaS, bacteria were cultured at 30° C. for 20 h.

Transmission Electron Microscopy (TEM).

Newman or Newman ΔtarO were inoculated to approximately $10^9$ CFU/mL in TSB containing 10 mg/L Congo Red, and cultured at 37° C. for 6 h. Cells were collected at 0 or 6 h, fixed in Karnovsky's fixative (2% paraformaldehyde and 2.5% glutaraldehyde in cacodylate buffer [pH 7.4]), and processed for TEM using standard procedures described in Suzuki et al. (*Invest. Ophthalmol. Vis. Sci.* 52:3187-3192, 2011). For TEM, 60- to 90-Å sections were obtained, viewed, and photographed with a transmission electron microscope (model 410; Philips Electronics NV, Eindhoven, The Netherlands).

Synergy Between Congo Red and Tunicamycin.

A standard checkerboard assay, using Congo Red and tunicamycin, was performed as described in Lorian (Antibiotics in Laboratory Medicine, 4th Edition, Baltimore, Md., Williams & Wilkins Co., 1996). To assess the kinetics of inhibition, cultures of strain Newman were started in TSB containing either Congo Red or tunicamycin. Briefly, an overnight culture of *S. aureus* strain Newman was diluted to approximately $10^5$ CFU/mL in 10 mL of TSB containing 10 mg/L Congo Red or 1 mg/L tunicamycin, and cultured at 37° C. statically. Following 2 h incubation, tunicamycin (1 mg/L final concentration) was added to the Congo Red culture, or Congo Red (10 mg/L final concentration) was added to the tunicamycin culture. Following 6 h of additional incubation bacteria were enumerated by plating serial ten-fold dilutions.

*Caenorhabditis elegans* Infection.

*C. elegans* glp-4(bn2); sek-1(km4) was used for all experiments and infected essentially as described in Breger et al. (*PLoS Pathog.* 3:e18, 2007), with minor modifications. This mutant line was selected for liquid assay experiments because they are unable to produce progeny at 25° C. (Miyata et al., *Genetics* 178:903-918, 2008), and the deleted sek-1 gene encodes a conserved mitogen-activated protein (MAP) kinase involved in innate immunity (Kim et al., *Science* 297:623-626, 2002), expediting the rate of killing. Worms were cultured and maintained on nematode growth medium (NGM) agar containing lawns of *E. coli* HB101 (Breger et al., *PLoS Pathog.* 3:e18, 2007).

To assess the sensitivity of *C. elegans* to infection by *S. aureus* RN6390 or an isogenic ΔtarO strain, the bacteria were cultured in TSB at 37° C. Overnight cultures were plated onto 10 cm TSB agar plates for 18 hours at 37° C., and cooled at room temperature for 30 minutes. Washed young adult worms were infected on lawns of *S. aureus* strains for 3 hours at 25° C. After washing three times with M9, worms were transferred into the wells of a six well microtiter plates (40 worms per well). Each well contained 2 mL of assay medium (20% BHI: 80% M9 v/v) containing various concentrations of Congo Red, tunicamycin, or a combination of Congo Red and tunicamycin. The plates were incubated at 25° C., and examined for viability at 24 hour intervals for 9 days using a Nikon SMZ645 dissecting microscope. Biological replicates of each experiment were conducted.

Statistical Analysis.

Differences in *C. elegans* survival were tested for significance by Kaplan-Meier and log-rank test (STATA6; STATA, College Station, Tex.). $P<0.05$ was considered as significant.

Results

Antimicrobial Activity of Congo Red Against Teichoic Acid-Deficient Mutants.

Figures 3A, 3B:
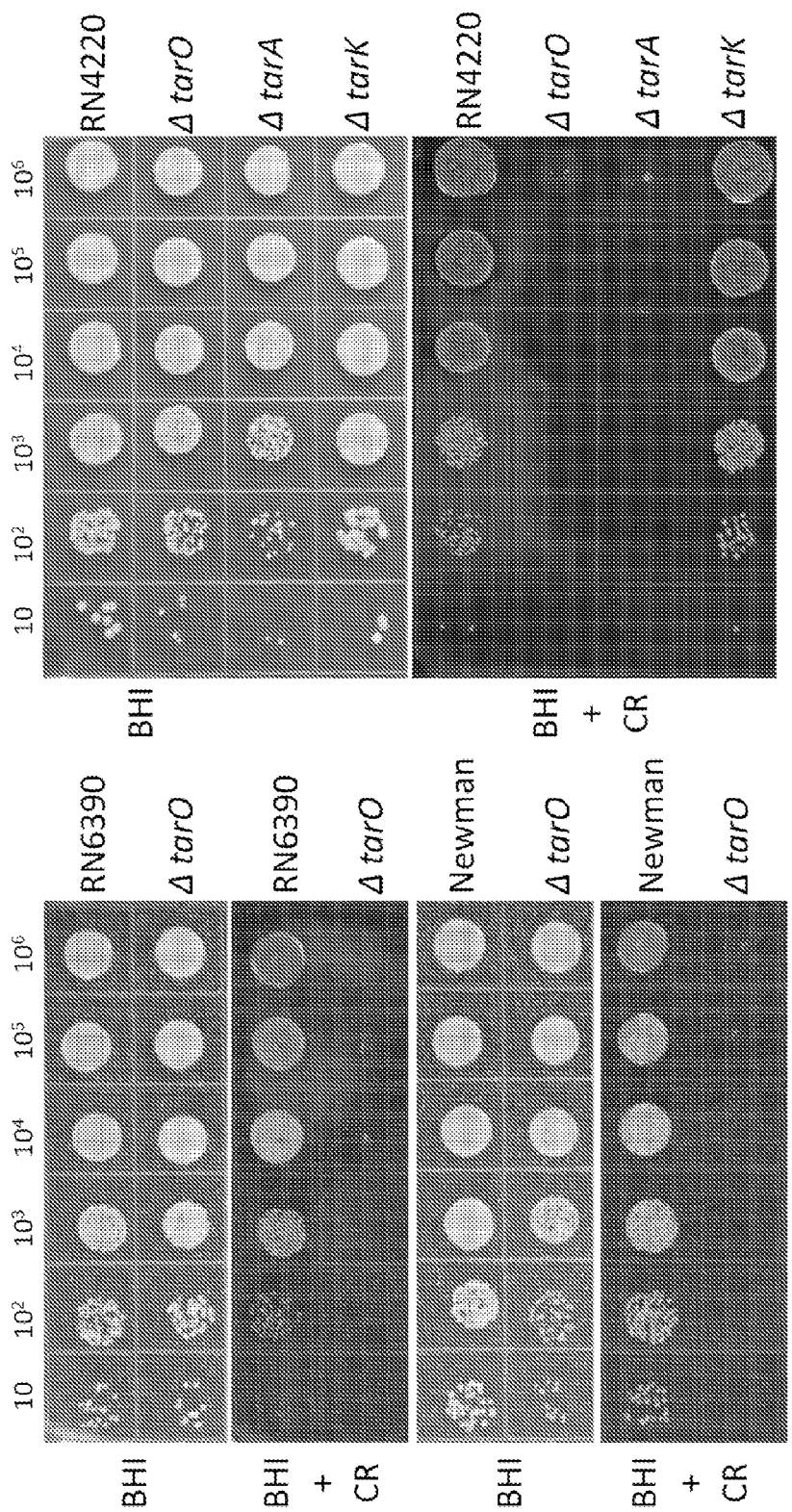
FIG. 3A is pictures showing the growth of S. aureus RN6390 and Newman, and mutant strains of S. aureus RN6390 and Newman on brain heart infusion (BHI) agar or BHI agar supplemented with 0.08% (w/v) Congo Red (BHI+CR). All plates were inoculated with 10 to $10^6$ cells of each strain, and photographed after 24 hours incubation at 37° C. Genotypes are indicated on the left side of the figure.
FIG. 3B is pictures showing the growth of S. aureus RN6390 and mutant strains on BHI agar (BHI) or BHI agar supplemented with 0.08% (w/v) Congo Red (BHI+CR). All plates were inoculated with 10 to $10^6$ cells of each strain, and photographed after 24 hours incubation at 37° C. Genotypes are indicated on the left side of the figure.

High throughput screening recently identified several inhibitors of *S. aureus* wall teichoic acid (WTA) biosynthesis (Swoboda et al., *ACS Chem. Biol.* 4:875-883, 2009). The strategy involved screening in parallel a 55,000-compound library against wild type and ΔtarO *S. aureus* to identify compounds in that selectively inhibited the growth of the wild type, but not the mutant, strain. Three compounds were identified that specifically lacked activity against the tarO mutant, suggesting they targeted irreversible reactions downstream in the biosynthesis of WTA. In examining the virulence (Suzuki et al., *Invest, Ophthalmol. Vis. Sci.* 52:3187-3192, 2011) and other properties of cells blocked in WTA biosynthesis, a tarO WTA-less mutant was discovered to be highly susceptible to Congo Red (FIG. 3A). To confirm the importance of WTA in this phenotype, and to determine the relationship between the point on the WTA pathway blocked and Congo Red sensitivity, tarA and tarK mutants were also assessed. Although neither tarA nor tarO strains grew on agar containing 0.08% w/v Congo Red, growth of the tarK strain was not affected (FIG. 3B). A tarK deletion produces a substantial amount of long chain WTA polymer because tarL compensates (Meredith et al., *J. Bacteriol.* 190:3046-3056, 2008).

Figures 4A, 4B:
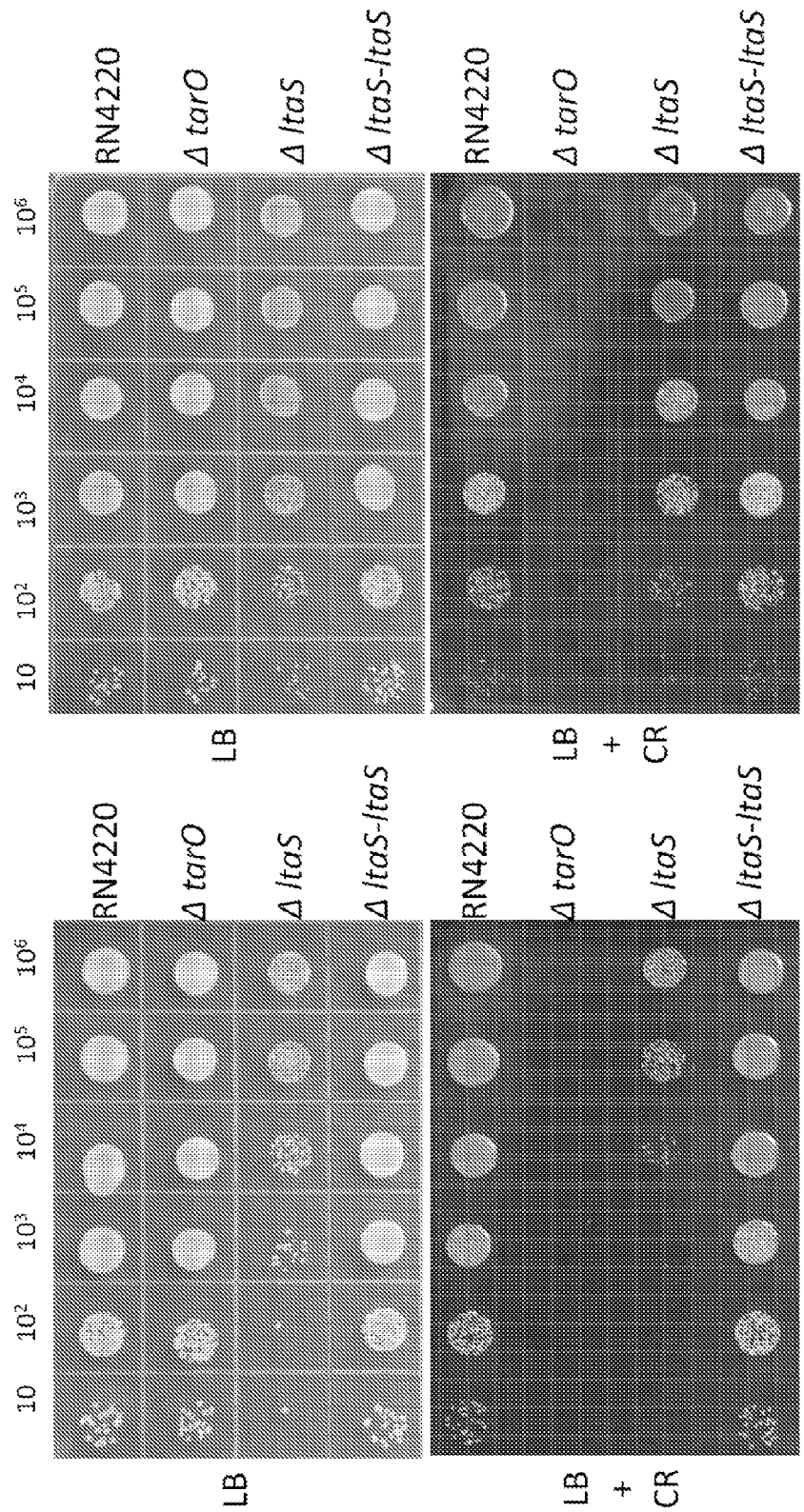
FIG. 4A is pictures showing the growth of S. aureus RN4220 and isogenic mutant strains on Luria-Bertani (LB) agar or LB agar supplemented with 0.08% (w/v) Congo Red (LB+CR). All plates were inoculated with 10 to $10^6$ cells of each strain, and photographed after 24 hours incubation at 37° C. Genotypes are indicated on the left side of the figure.
FIG. 4B is pictures showing the growth of S. aureus RN4220 and isogenic mutant strains on LB agar or LB agar supplemented with 0.08% (w/v) Congo Red (LB+CR). All plates were inoculated with 10 to $10^6$ cells of each strain, and photographed after 24 hours incubation at 30° C. Genotypes are indicated on the left side of the figure.

To determine whether loss of lipoteichoic acid (LTA) could also generate the Congo Red susceptible phenotype, an ltaS mutant of *S. aureus* was tested (Oku et al., *J. Bacteriol.* 191:141-151, 2009). The ltaS mutant is sensitive to heat and low osmolarity (Grundling et al., *Proc. Natl. Acad. Sci. U.S.A.* 104:8478-8483, 2007; Oku et al., *J. Bacteriol.* 191:141-151, 2009). Therefore, Congo Red was added at 0.08% w/v to Luria broth (LB) agar (having a higher NaCl concentration than BHI), and the strain was tested for Congo Red sensitivity at 30° C. To determine whether the Congo Red effect was temperature related, the ltaS mutant was retested at 37° C., where it grows slowly (FIGS. 4A and 4B). In either case, Congo Red had no effect on the ltaS mutant (FIGS. 4A and 4B). In contrast, the tarO mutant was inhibited by Congo Red at both 30° C. and 37° C. (FIGS. 4A and 4B).

Minimum inhibitory concentrations (MICs) for Congo Red were determined by microdilution assay. Consistent with the results of agar plate tests, the parental strain RN4220, and isogenic tarK, and ltaS mutants, as well as an ltaS strain complemented on a multicopy plasmid, were all resistant to Congo Red at concentrations>1024 mg/L (Table 2). In contrast, tarO and tarA mutants lacking WTA exhibited MICs 250-2000 fold lower (0.5 to 4 mg/L) (Table 2). To determine whether this was unique to the RN6390 lineage, which possesses several known mutations (Peng et al., *J. Bacteriol.* 170:4365-4372, 1988), wild type strain Newman was tested along with an isogenic tarO mutant. Again, the wild type exhibited an MIC>1024 mg/L, whereas the tarO mutant was sensitive to 1 mg/L (Table 1). Hence, the sensitizing effects of deleting tarO are general.

TABLE 2

In Vitro Activities of Congo Red Against Tested Strains

| S. aureus | MIC (mg/L) |
|---|---|
| RN6390 | >1024 |
| RN6390ΔtarO | 4 |
| RN4220 | >1024 |
| RN4220ΔtarO | 2 |
| RN4220ΔtarA | 0.5 |
| RN4220ΔtarK | >1024 |
| RN4220ΔltaS | >1024 |
| RN4220ΔltaS-ltaS | >1024 |
| Newman | >1024 |
| NewmanΔtarO | 1 |

Figure 5:
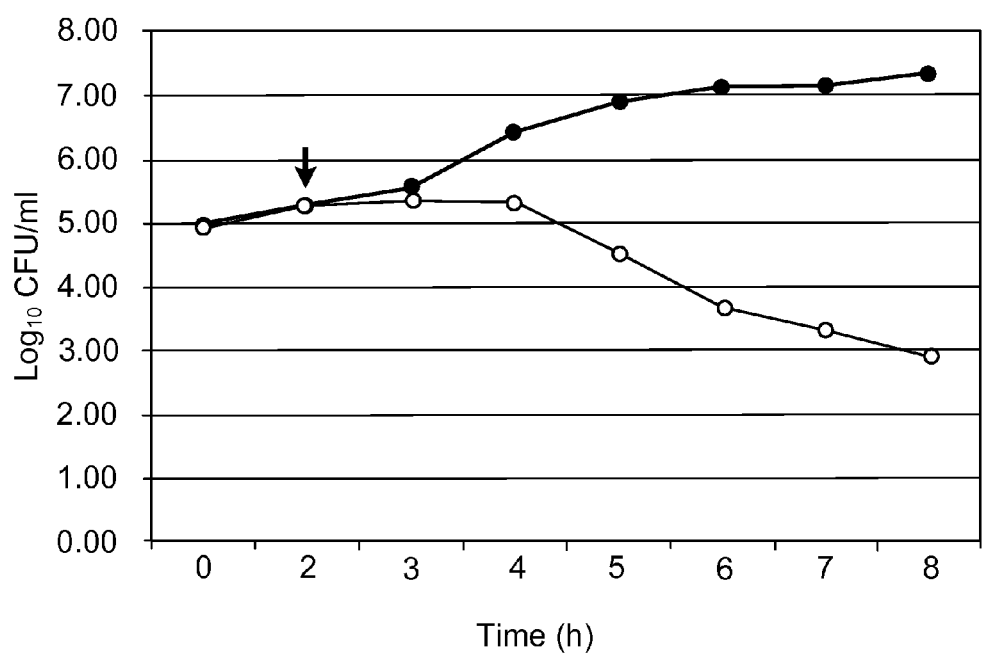
FIG. 5 is a graph showing the growth of S. aureus strain Newman (closed circles) and Newman ΔtarO (open circles) in tryptic soy broth (TSB) before and following the addition of 10 mg/L Congo Red (black arrow).
Figure 6:
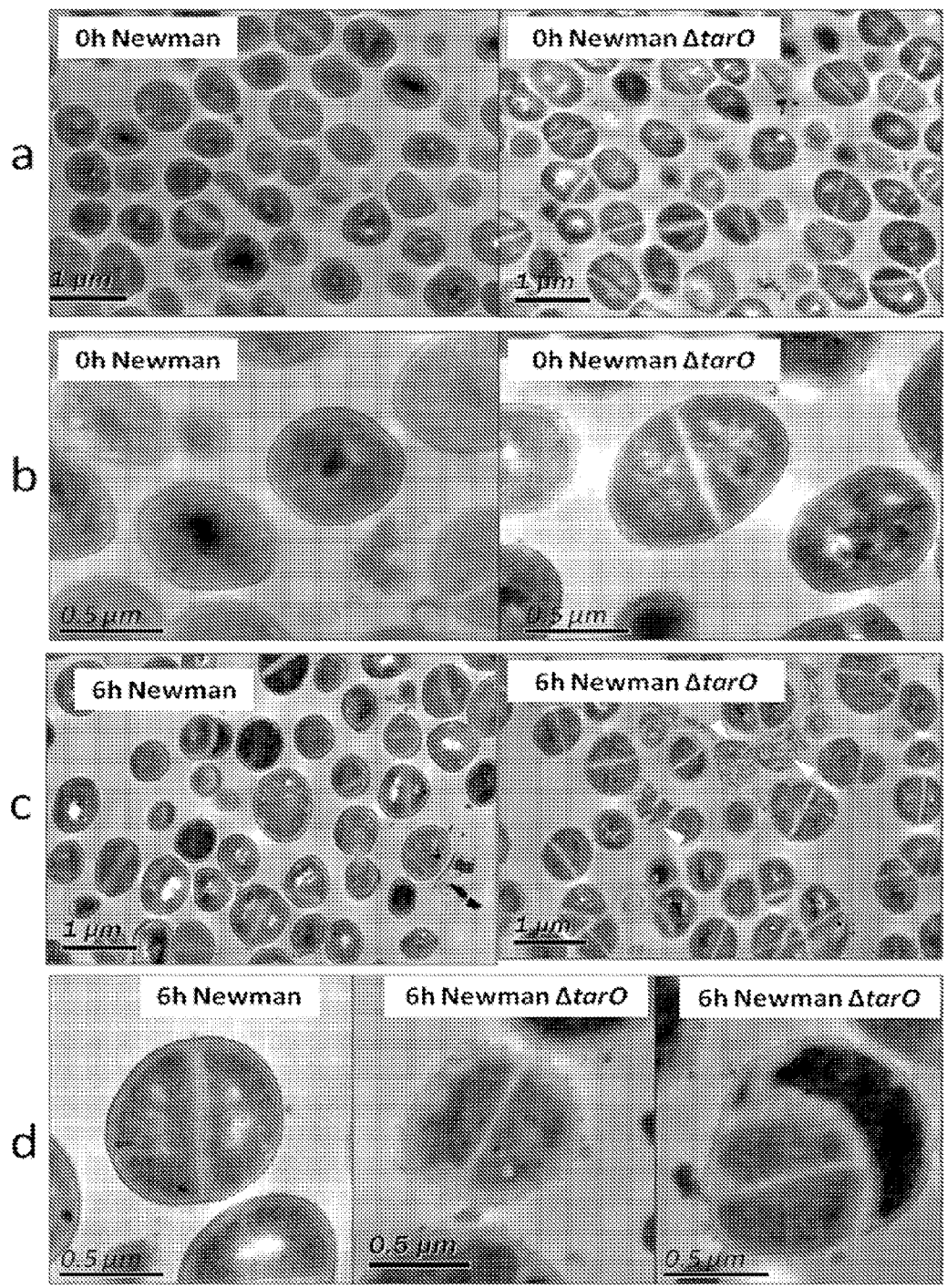
FIG. 6A is a set of two low magnification transmission electron micrographs of S. aureus strain Newman (left panel) and Newman ΔtarO (right panel) in TSB prior to incubation (0 hour) with 10 mg/L Congo Red.
FIG. 6B is a set of two high magnification transmission electron micrographs of S. aureus strain Newman (left panel) and Newman ΔtarO (right panel) in TSB prior to incubation (0 hour) with 10 mg/L Congo Red.
FIG. 6C is a set of two low magnification transmission electron micrographs of *S. aureus* strain Newman (left panel) and Newman ΔtarO (right panel) after 6 hours of culture in TSB supplemented with 10 mg/L Congo Red. Arrows indicate the lysis of the ΔtarO mutant at 6 hours (left panel).
FIG. 6D is a set of three high magnification transmission electron micrographs of *S. aureus* strain Newman (left panel) and Newman ΔtarO (center and right panels) after 6 hours of culture in TSB supplemented with 10 mg/L Congo Red. The cell wall of strain Newman ΔtarO was detectably thickened and altered at 6 hours (center panel). Abnormal septa were observed in the Newman ΔtarO strain at 6 hours (right panel).

To assess kinetics of Congo Red inhibition, growth of *S. aureus* strain Newman and its tarO mutant were assessed in TSB containing 10 mg/L Congo Red. Newman tarO began to die 3 hours after addition of Congo Red (FIG. 5). To probe the mechanism of killing, Congo Red-inhibited cells were examined by transmission electron microscopy (TEM) (FIGS. 6A-6D). In contrast to the parental strain, the WTA deficient mutant before exposure to Congo Red shows a rough surface with many protrusions (FIGS. 6A and 6B). Although morphology of the parental strain is not detectably affected after 6 hours of Congo Red treatment, the WTA deficient mutant at the same time point shows disruption and lysis, with some cells showing an aberrantly thickened cell wall (FIGS. 6C and 6D). Together, these results show that WTA, but not LTA, protects *S. aureus* from killing by Congo Red, even though both teichoic acids are composed of repetitive polyol phosphate subunits. Since Congo red contains two sulfonic-acid groups, the MICs for sulfanilamide which is developed from prontocil were determined in the Newman and tarO mutant strains. However, the MIC for either strains was >128 mg/L.

Figure 7:
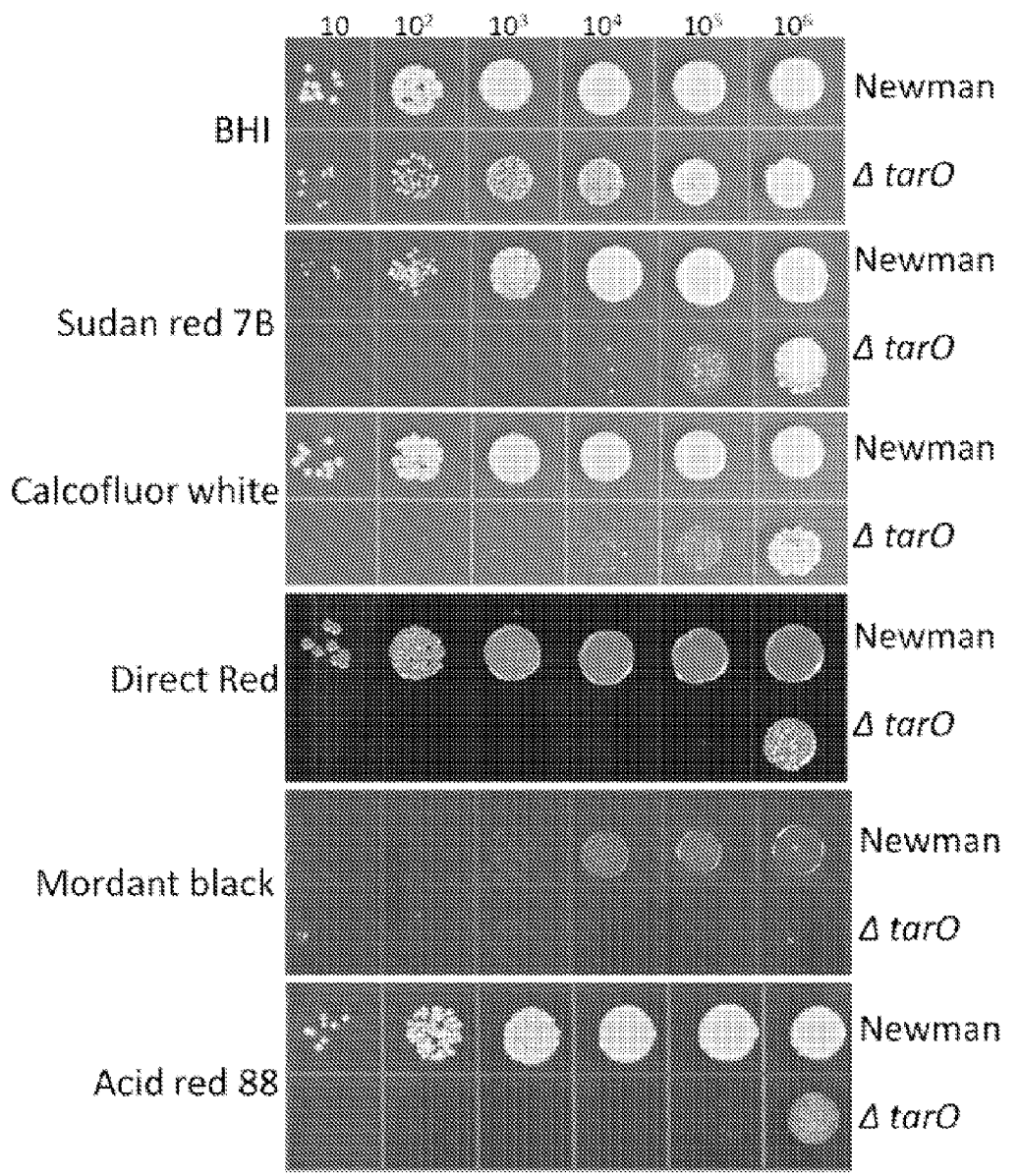
FIG. 7 is pictures showing the growth of wild type *S. aureus* strain Newman and Newman ΔtarO on BHI agar or BHI agar supplemented with 0.08% (w/v) Sudan Red 7B, 0.01% (w/v) Calcofluor White, 0.08% (w/v) Direct Red, 0.08% (w/v) Mordant Black, or 0.08% (w/v) Acid Red. All plates were inoculated with 10 to $10^6$ cells or each strain and incubated at 37° C. for 24 hours, and photographed. Genotypes are indicated on the left side of the figure.

To test whether the loss of WTA conferred susceptibility to other dyes of related structure, Sudan Red 7B (0.08% w/v), Calcofluor White (0.01% w/v), Direct Red (0.08% w/v), Mordant black (0.08% w/v), and Acid Red (0.08% w/v) were tested for the ability to selectively suppress growth of a tarO mutant, but not parental strain. Loss of WTA conferred susceptibility to each of these dyes (FIG. 7).

Tunicamycin and Congo Red are Highly Synergystic

Tunicamycin is an inhibitor of a large class of enzymes that couple sugar phosphates to membrane-embedded lipid phosphates, and it inhibits WTA production by blocking TarO, a WTA enzyme belonging to this class. However, tunicamycin has not been used extensively to treat infection because, as noted above, inhibitors of TarO are not lethal to *S. aureus* in vitro, and tunicamycin concentrations that block bacterial growth in vitro are toxic to eukaryotic cells (Price et al., *J. Antibiot.* (Tokyo), 60:485-491, 2007). One strategy for circumventing problems of toxicity and lack of cidality is to incorporate such drugs at subtoxic levels in a mixture with a synergistic compound. Therefore, to determine whether wild type *S. aureus* can be inhibited by a synergy between the ability of tunicamycin to inhibit WTA biosynthesis at low concentrations, and Congo Red, a two-dimensional checkerboard dilution series for each compound was performed. As predicted, Congo Red exhibited strong synergy with tunicamycin (FIG. 8A). Although the MIC of Congo Red against strain Newman as a single agent was >1024 mg/L, levels of tunicamycin as low as 5 mg/L reduced the Congo Red MIC to 1 mg/L (FIG. 8A).

To assess the rate of killing, and to obtain evidence for the mechanism of synergy, *S. aureus* strain Newman was grown in TSB in the presence of either 10 mg/L of Congo Red or 1 mg/L of tunicamycin (values well below the individual MICs). Following a 2-hour incubation, the alternate compound was added to the culture and the effect on growth was assessed. When Congo Red was added at a level of 10 mg/L to the tunicamycin culture, bacterial death was noticeable 2 hours later (FIG. 8B). However, when tunicamycin was added at 1 mg/L following 2 hours of culture in Congo Red, killing was only apparent after 4 hours of incubation (FIG. 8C). This implies that 4 hours of growth in the presence of tunicamycin is required to deplete WTA levels to the point where the cell becomes susceptible to Congo Red killing. These results suggest that a mixture of Congo Red and tunicamycin, could have excellent antimicrobial activity against gram positive bacteria (e.g., *S. aureus*).

Efficacy of Congo Red or Tunicamycin In Vivo

As a proof of principle to determine whether the synergistic activity of Congo Red and tunicamycin could be exploited therapeutically using concentrations below levels that exhibit toxicity, the well-studied nematode *Caenorhabditis elegans* infection model was employed (Garsin et al., *Proc. Natl. Acad. Sci. U.S.A.* 98:10892-10897, 2001). Previous reports showed that *C. elegans* infected with lethal doses of several human pathogens can be cured by treatment with conventional and novel antibiotics. Therefore Congo Red or tunicamycin, or combinations thereof, were first tested for toxicity against uninfected *C. elegans*. Tunicamycin exhibits dose dependent toxicity, mirroring what has been found in mammals (Morin et al., *Cancer Res.* 43:1669-1674, 1983). Congo Red showed little toxicity for *C.*

Figure 9A:
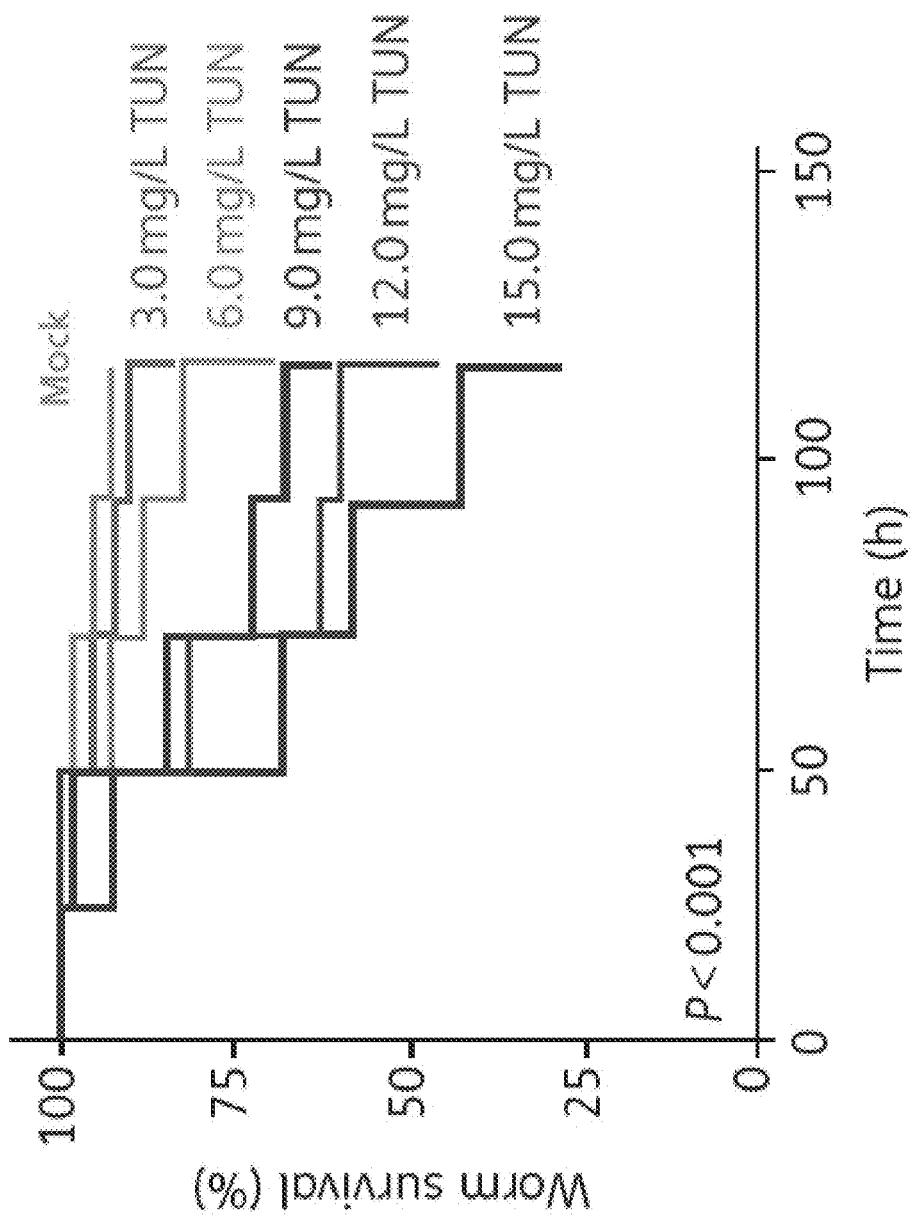
FIG. 9A is a graph showing the toxicity of 6.25 mg/L to 100.0 mg/L tunicamycin for *C. elegans* (n=40 per well). In pairwise comparison log rank tests, the difference in survival curves between mock and each treatment was $p<0.01$.
Figure 9C:
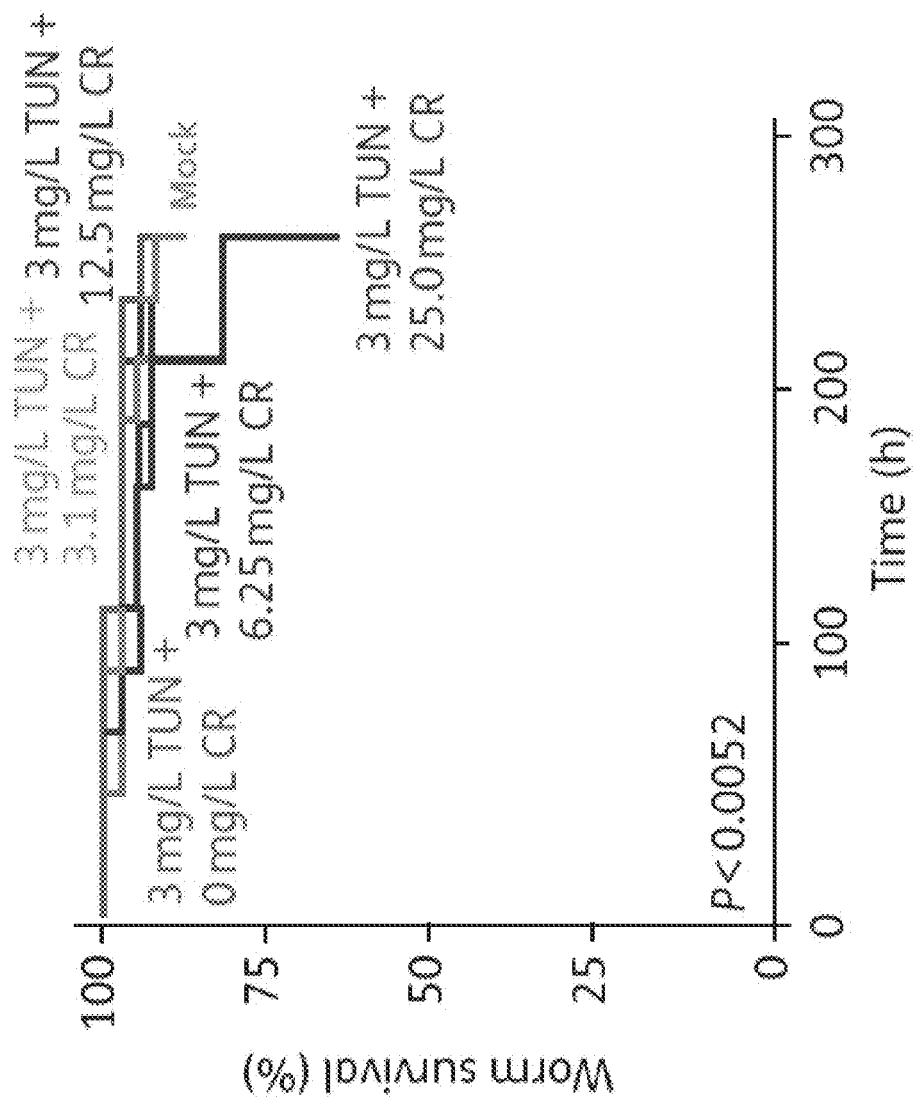
FIG. 9C is a graph showing the toxicity of the combination of 3 mg/L tunicamycin and 3.1 mg/L to 25.0 mg/L Congo Red for *C. elegans* (n=40 per well). In pairwise comparison log rank tests, the difference in survival curves between mock and each treatment was $p<0.01$.
Figure 9D:
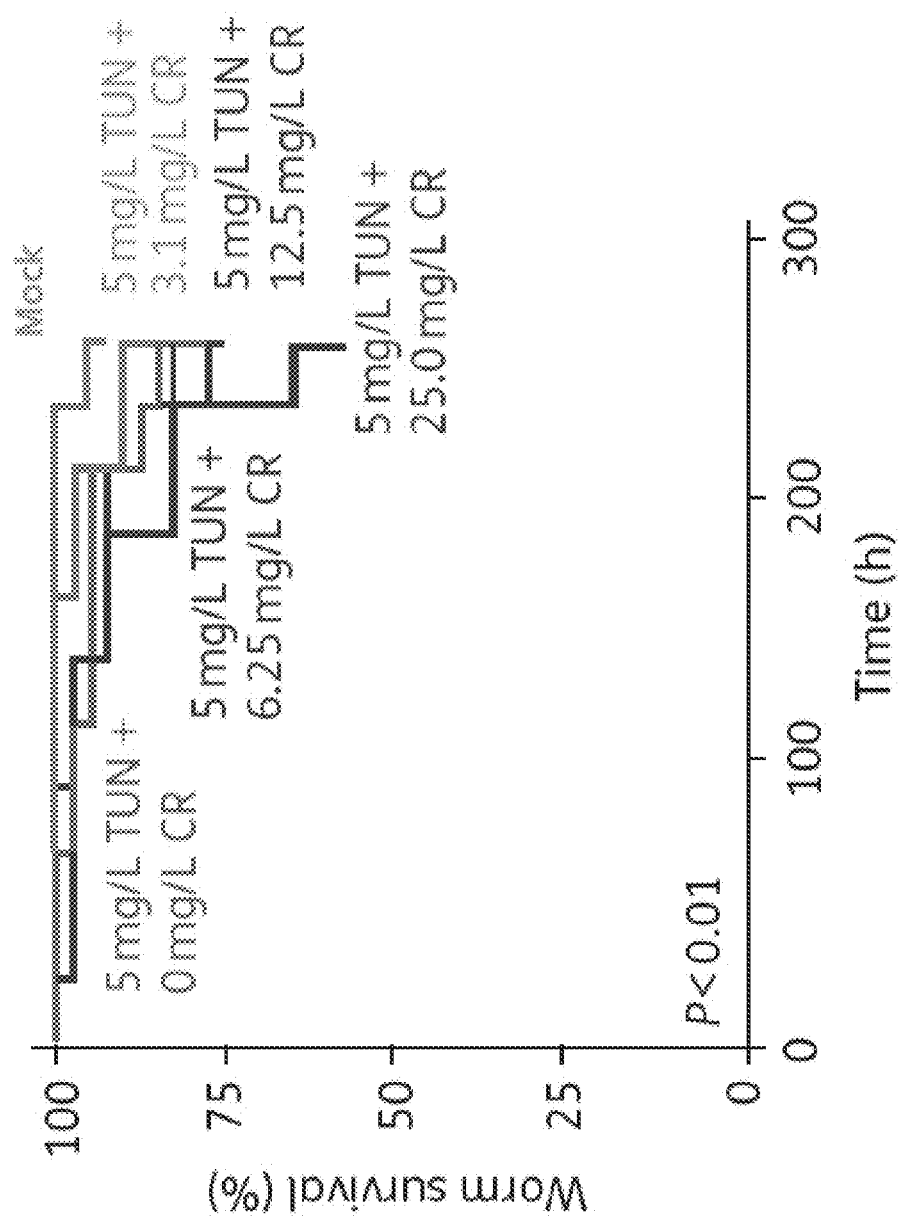
FIG. 9D is a graph showing the toxicity of the combination of 5 mg/L tunicamycin and 3.1 mg/L to 25.0 mg/L Congo Red for *C. elegans* (n=40 per well). In pairwise comparison log rank tests, the difference in survival curves between mock and each treatment was $p<0.01$.

*elegans*, even at comparatively high concentrations (FIGS. 9A and 9B). The compound combination also shows toxicity at higher concentrations of Congo Red and tunicamycin (FIGS. 9C and 9D). In toxicity tests, a combination of less than 12.5 mg/L Congo Red and 3 or 5 mg/L tunicamycin does not show strong toxicity against *C. elegans*.

Figure 10A:
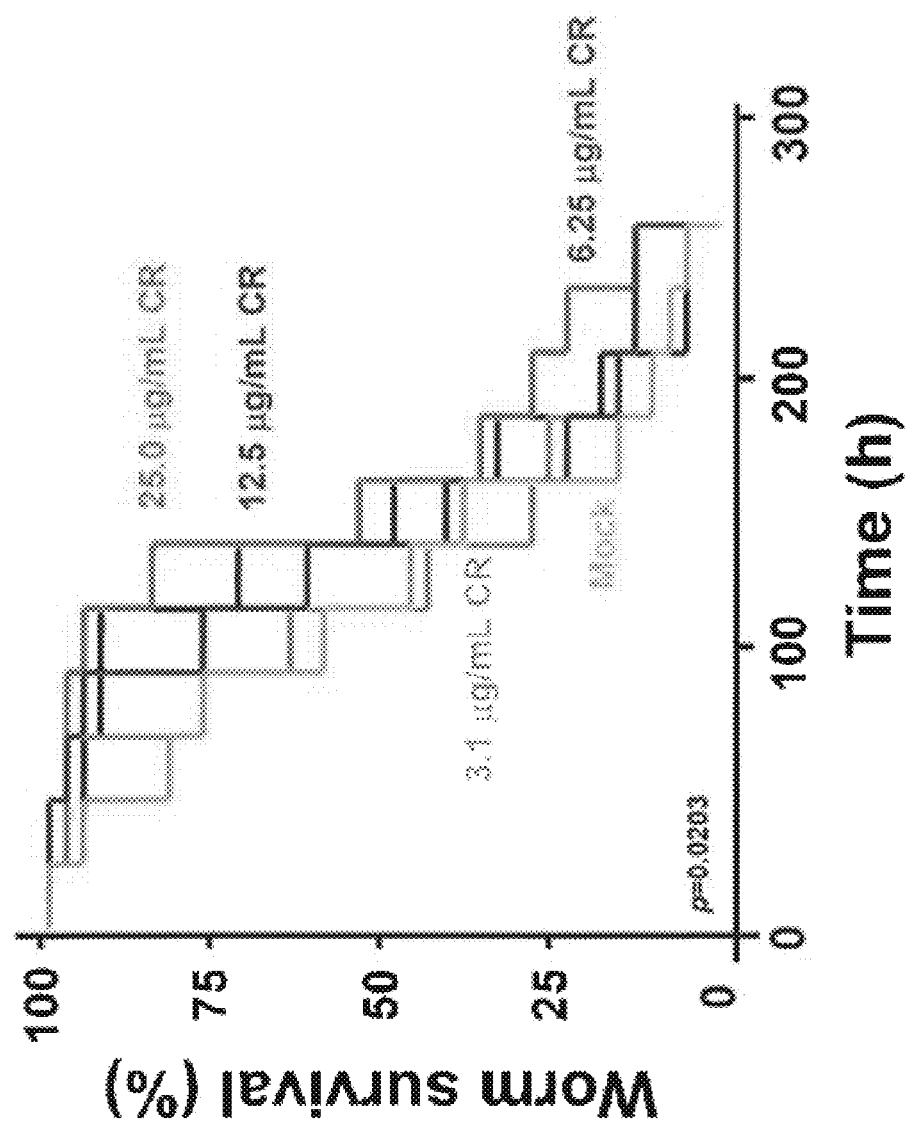
FIG. 10A is a graph showing the inability of Congo Red at 3.1 mg/L, 6.25 mg/L, 12.5 mg/L, or 25.0 mg/L to rescue nematodes infected with *S. aureus* RN6390.
Figure 10B:
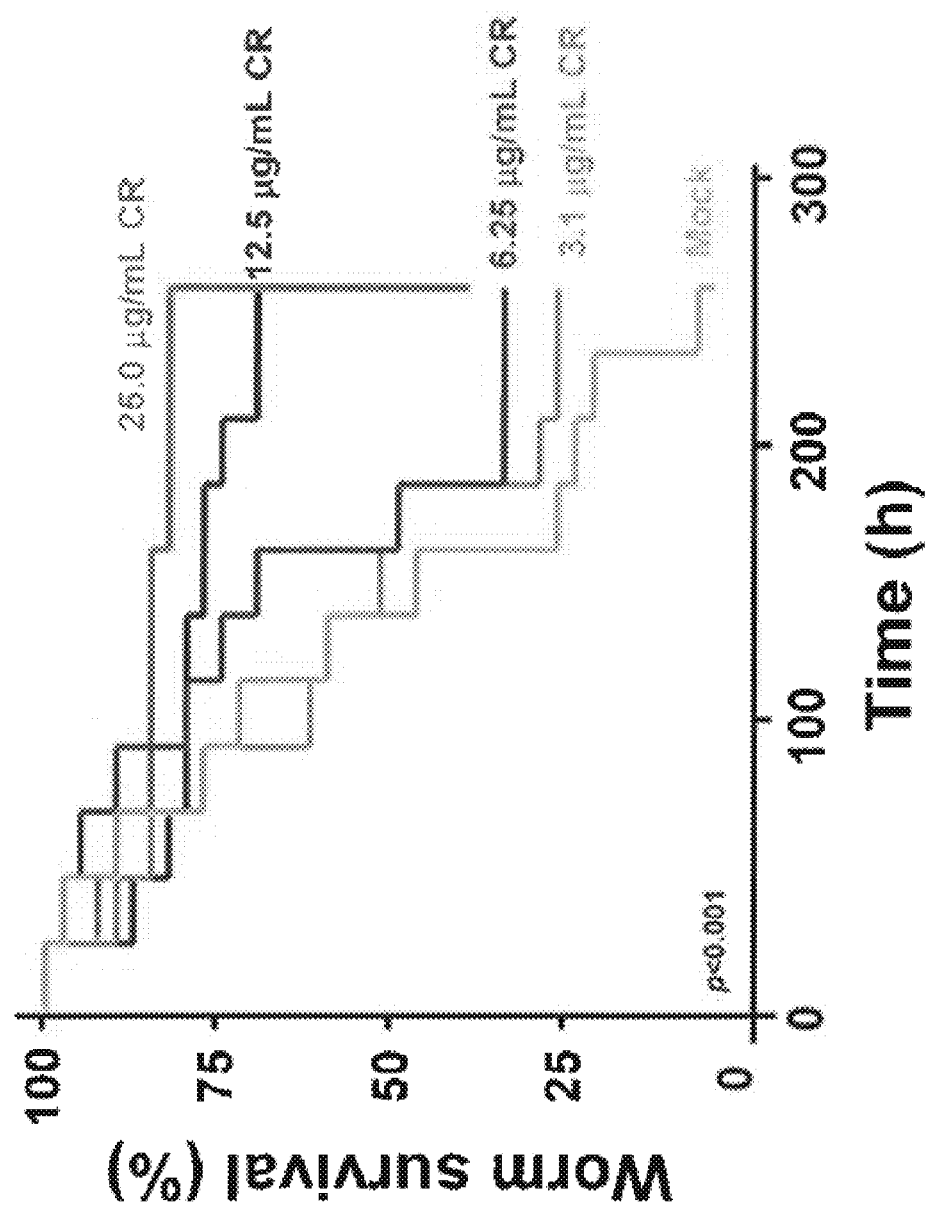
FIG. 10B is a graph showing the ability of Congo Red at 3.1 mg/L, 6.25 mg/L, 12.5 mg/L, or 25.0 mg/L to rescue nematodes infected with *S. aureus* RN6390 ΔtarO in a concentration dependent manner.

Next, *C. elegans* was infected with *S. aureus* RN6390, or with WTA deficient RN6390 ΔtarO. While Congo Red had little effect on *C. elegans* infected with RN6390 (FIG. 10A), nematodes infected with RN6390 ΔtarO were rescued by Congo Red in a concentration dependent manner (FIG. 10B), illustrating the potential for Congo Red to cure infections caused by *S. aureus* genetically lacking WTA in vivo (FIG. 10B).

Figure 10C:
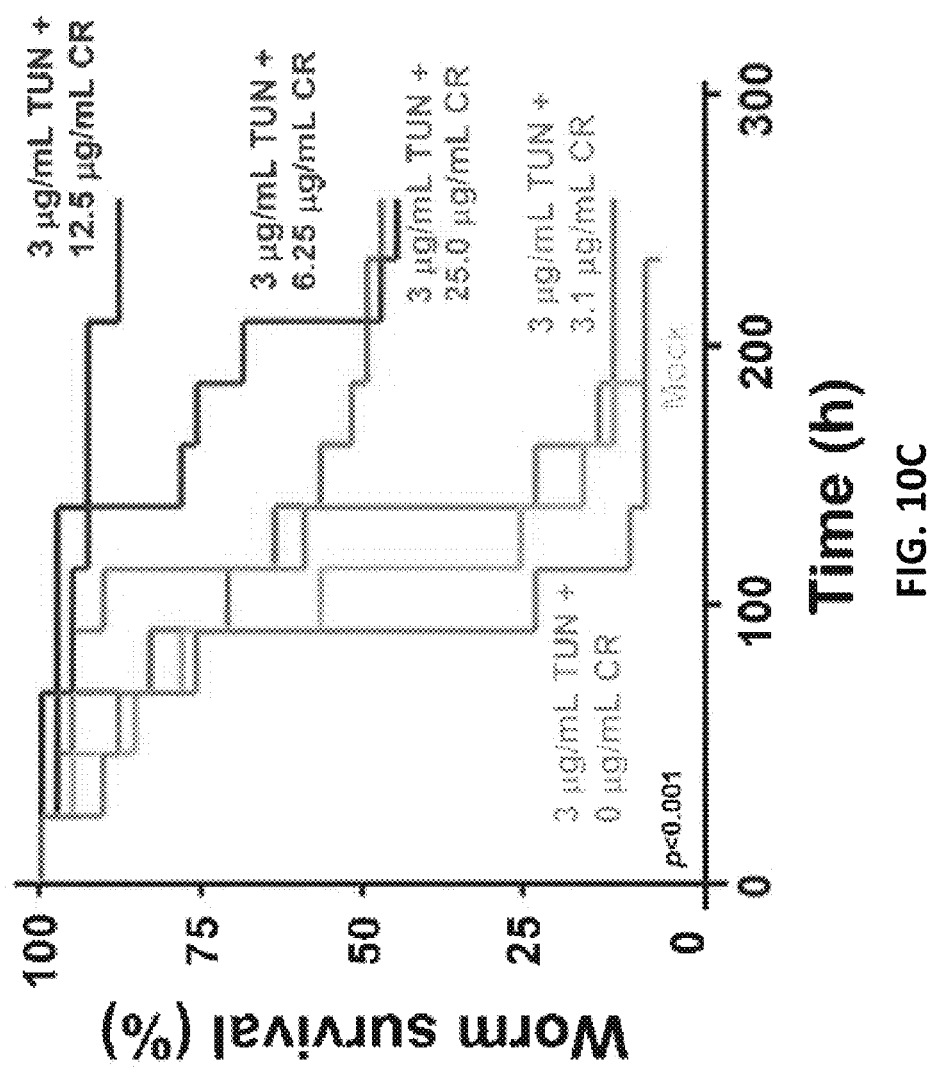
FIG. 10C is a graph showing the ability of 3 mg/L tunicamycin and 3.1 mg/L, 6.25 mg/L, 12.5 mg/L, or 25.0 mg/L Congo Red to rescue nematodes infected with *S. aureus* RN6390. In pairwise comparison log rank tests, the difference in survival curves between mock and combination therapy treatments was $p<0.001$.
Figure 10D:
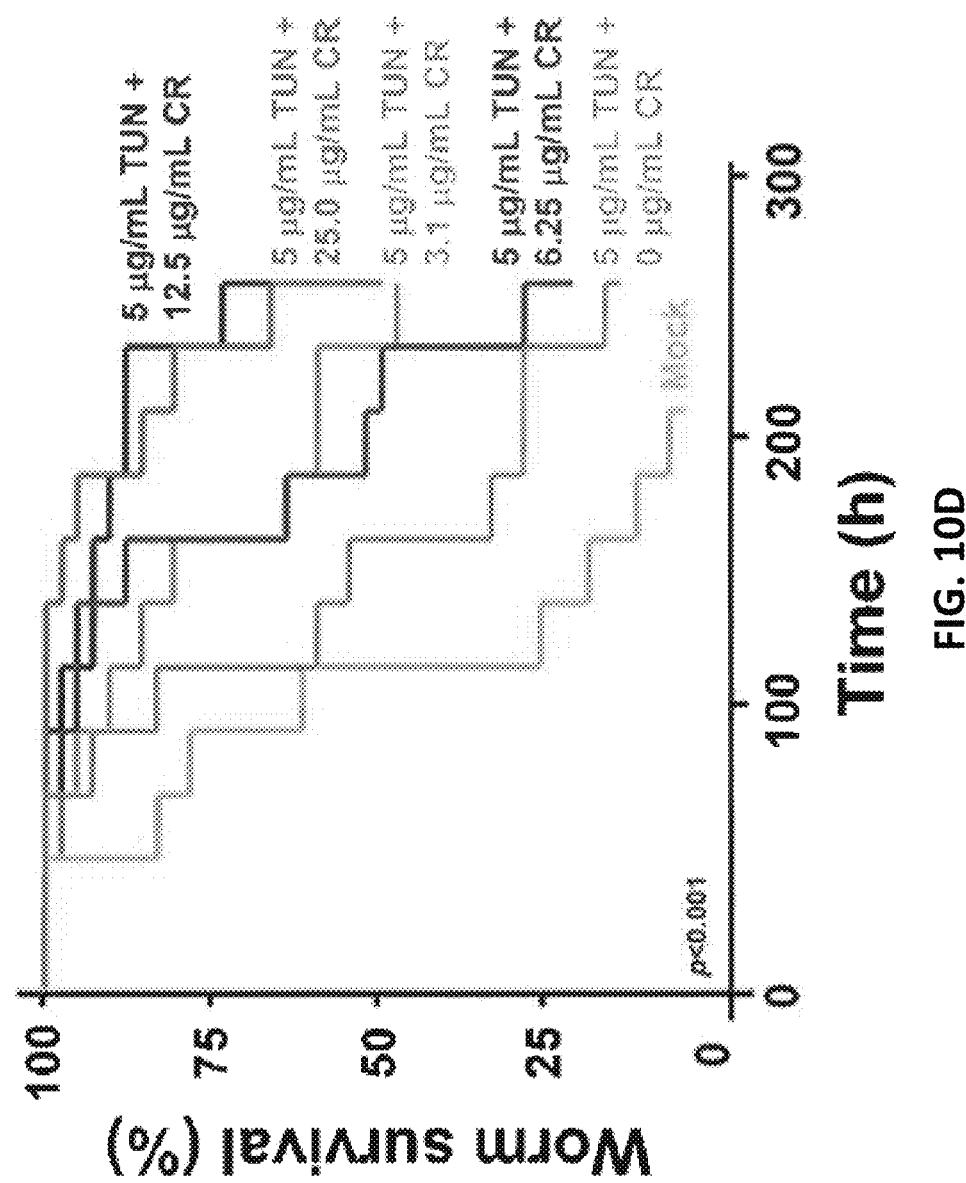
FIG. 10D is a graph showing the ability of 5 mg/L tunicamycin and 3.1 mg/L, 6.25 mg/L, 12.5 mg/L, or 25.0 mg/L Congo Red to rescue nematodes infected with *S. aureus* RN6390. In pairwise comparison log rank tests, the difference in survival curves between mock and combination therapy treatments was $p<0.001$.

Next, synergistic combinations of Congo Red and tunicamycin were tested. Treatment with a synergistic combination produced a significant curative effect in a Congo Red concentration dependent manner ($P<0.001$ for treatments compared to mock or tunicamycin only) (FIGS. 10C and 10D), providing proof of principle for the strategy of blocking WTA biosynthesis while also treating *S. aureus* with a compound to which it is now rendered highly susceptible.

In sum, these data show that combinations of an azo dye and a TarO inhibitor are capable of inducing cell death in a gram positive bacterium and decreasing proliferation of a gram positive bacterium. In addition, these data indicate that the combination of an azo dye and a TarO inhibitor can be used to treat a subject having a gram positive bacterial infection.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for inducing cell death in a gram positive bacterium or reducing the proliferation of a gram positive bacterium, the method comprising contacting a gram positive bacterium with Congo Red and tunicamycin in amounts sufficient to induce cell death in the gram positive bacterium or amounts sufficient to reduce the proliferation of the gram positive bacterium.

2. The method of claim 1, wherein the gram positive bacterium is present in a mammal.

3. The method of claim 1, wherein the gram positive bacterium is present in vitro.

4. The method of claim 3, wherein the gram positive bacterium is present in a cell culture, is present in or on a food composition, or is present in a pharmaceutical or cosmetic composition.

5. The method of claim 1, wherein the gram positive bacterium is a *coccus* gram positive bacterium.

6. The method of claim 5, wherein the *coccus* gram positive bacterium is from the *Streptococcus*, *Enterococcus*, or *Staphylococcus* genus.

7. The method of claim 1, wherein the gram positive bacterium is a *bacillus* gram positive bacterium.

8. The method of claim 7, wherein the *bacillus* gram positive bacterium is from the *Cornebacterium*, *Listeria*, *Bacillus*, or *Clostridium* genus.

9. A method of treating a subject having a gram positive bacterial infection, the method comprising administering to the subject having a gram positive bacterial infection Congo Red and tunicamycin in amounts sufficient to decrease the population of gram positive bacteria in the subject.

10. The method of claim 9, wherein the population of gram positive bacteria comprises *coccus* gram positive bacteria.

11. The method of claim 10, wherein the *coccus* gram positive bacteria are from the *Streptococcus*, *Enterococcus*, or *Staphylococcus* genus.

12. The method of claim 9, wherein the population of gram positive bacteria comprises *bacillus* gram positive bacteria.

13. The method of claim 12, wherein the *bacillus* gram positive bacteria are from the *Cornebacterium*, *Listeria*, *Bacillus*, or *Clostridium* genus.

14. The method of claim 1, wherein the concentration of Congo Red is less than 1024 mg/L.

15. The method of claim 9, wherein the amount of the tunicamycin is not toxic to the subject.

* * * * *

UNITED STATES PATENT AND TRADEMARK OFFICE
CERTIFICATE OF CORRECTION

PATENT NO. : 9,913,854 B2
APPLICATION NO. : 14/388685
DATED : March 13, 2018
INVENTOR(S) : Michael S. Gilmore and Takashi Suzuki Page 1 of 1

It is certified that error appears in the above-identified patent and that said Letters Patent is hereby corrected as shown below:

In Column 28, Line 21, in Claim 8, delete "*Cornebacterium*" and insert --Corynebacterium--

Signed and Sealed this
Twenty-third Day of October, 2018

Andrei Iancu
*Director of the United States Patent and Trademark Office*